(12) United States Patent
Dolle et al.

(10) Patent No.: US 6,852,713 B2
(45) Date of Patent: Feb. 8, 2005

(54) LACTAM DERIVATIVES AND METHODS OF THEIR USE

(75) Inventors: Roland E. Dolle, King of Prussia, PA (US); Paul Anson Tuthill, Newark, DE (US)

(73) Assignee: Adolor Corporation, Exton, PA (US)

( * ) Notice: Subject to any disclaimer, the term of this patent is extended or adjusted under 35 U.S.C. 154(b) by 0 days.

(21) Appl. No.: 10/414,802

(22) Filed: Apr. 16, 2003

(65) Prior Publication Data

US 2004/0209857 A1 Oct. 21, 2004

(51) Int. Cl.[7] .................... C07D 225/02; C07D 267/22; C07D 281/02; C07D 403/00; A61K 31/395
(52) U.S. Cl. .............................. 514/210.2; 514/212.08; 514/217.03; 514/326; 514/422; 540/451; 540/454; 540/463; 540/488; 540/525
(58) Field of Search ................................. 540/451, 454, 540/463, 488, 525; 514/210.2, 212.08, 217.03, 326, 422

(56) References Cited

U.S. PATENT DOCUMENTS

| | | | |
|---|---|---|---|
| 4,065,573 A | 12/1977 | Lednicer ..................... | 424/278 |
| 4,098,904 A | 7/1978 | Szmuszkovicz ............. | 424/324 |
| 4,145,435 A | 3/1979 | Szmuszkovicz ............. | 424/274 |
| 4,212,878 A | 7/1980 | Lednicer et al. ............ | 424/274 |
| 4,359,476 A | 11/1982 | Kaplan et al. ............... | 424/274 |
| 4,438,130 A | 3/1984 | Kaplan ........................ | 424/274 |
| 4,663,343 A | 5/1987 | Horwell et al. ............. | 514/429 |
| 4,906,655 A | 3/1990 | Horwell et al. ............. | 514/422 |
| 5,109,135 A | 4/1992 | D'Ambra et al. ............. | 544/73 |
| 5,242,944 A | 9/1993 | Park et al. ................... | 514/466 |
| 5,345,943 A | 9/1994 | Hargreaves et al. ........ | 128/742 |
| 5,369,131 A | 11/1994 | Poli et al. ................. | 514/772.4 |
| 5,434,292 A | 7/1995 | Saita et al. ................... | 560/51 |
| 5,532,266 A | 7/1996 | Gottschlich et al. ........ | 514/428 |
| 5,688,955 A | 11/1997 | Kruse et al. ............. | 546/276.4 |
| 5,804,595 A | 9/1998 | Portoghese et al. ......... | 514/428 |
| 6,177,438 B1 | 1/2001 | Nagase et al. .............. | 514/280 |

OTHER PUBLICATIONS

Andreev, N., et al., "Opioids suppress spontaneous activity of polymodal nociceptors in rat paw skin induced by ultraviolet irradiation," *Neurosci.*, 1994, 58(4), 793–798.
Antonijevic, I., et al., "Perineurial defect and peripheral opioid analgesia in inflammation," *J. Neurosci.*, Jan. 1995, 15(1), 165–172.
Barber, A., et al., "Opioid agonists and antagonists: an evaluation of their peripheral actions in inflammation," *Med. Res. Rev.*, 1992, 12(5), 525–562.
Buschmann, H., et al., *Analgesics*, Wiley–VCH, Verlag GMbH & Co. KgaA, Weinheim, 2002.
Flynn, G.L., "Mechanism of percutaneous absorption from physicochemical evidence," *Mechanism of Percutaneous Absorption*, Bronaugh, R.L., et al. (Eds.), 1985, 17–42.

Greene, T.W., et al., *Protective Groups in Organic Synthesis*, 2nd Ed., Wiley & Sons, 1991.
Handwerker, et al., *Pain and Inflammation*, Bond, et al. (Eds.), *Proceedings of the VIth World Congress on Pain*, Elsevier Science Publishers BV, 1991, Chap. 7, 59–70.
Hargreaves, J.M., et al., "The peripheral analgesic effects of opioids," *APS Journal*, 1993, 2(1), 51–59.
Hassan, A.H.S., et al., "Inflammation of the rat paw enhances axonal transport of opioid receptors in the sciatic nerve and increases their density in the inflamed tissue," *Neuroscience*, 1993, 55(1), 185–195.
Iyengar, S., et al., "Kappa opiate agonists modulate the hypothalamic–pituitary–adrenocortical axis in the rat," *J. Pharmacol. & Exp. Ther.*, 1986, 238(2), 429–436.
Jain, K.K., "A guide to drug evaluation for chronic pain," *Emerging Drugs*, 2000, 5(2), 241–257.
Larock, R.C., "Comprehensive Organic Transformations, A Guide to Functional Group Preparations" *VCH Publishers, Inc.*, 1989, 432–434.
Leander, J.D., et al., "Diuresis and suppression of vasopressin by Kappa opioids: comparison with Mu and Delta opioids and clonidine," *J. Pharmacol. Exp. & Ther.*, 1985, 234(2), 463–469.
Lutz, R.A., et al., "Opioid receptors and their pharmacological profiles," *J. of Recept. Res.*, 1992, 12(3), 267–286.
Mansour, A., et al., "Anatomical distribution of opioid receptors in mammalians: An overview," *Opioid I*, Herz, A. (Ed.), 1993, Chap. 5, 79–105.
Manzanares, J., et al., "Kappa–opioid–receptor–mediated regulation of α–melanocyte–stimulating hormone secretion and tuberohypophysial dopaminergic neuronal activity," *Neuroendocrinology*, 1990, 52, 200–205.
Millan, M.J., "κ–opioid receptors and analgesia," *Trends Pharmacol. Sci.*, Feb. 1990, 11, 70–76.
Morley, J.E., et al., "Involvement of dynorphin and the kappa opioid receptor in feeding," *Peptides*, 1983, 4, 797–800.

(List continued on next page.)

Primary Examiner—Bruck Kifle
(74) Attorney, Agent, or Firm—Woodcock Washburn LLP

(57) ABSTRACT

Lactam derivatives of the general formula

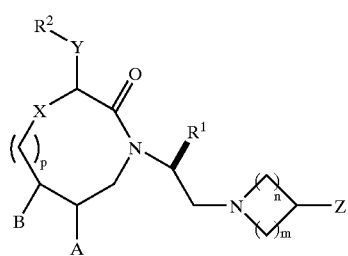

are disclosed. Pharmaceutical compositions containing the compounds and methods for their use are also disclosed.

48 Claims, No Drawings

OTHER PUBLICATIONS

Neugebauer, V., et al., "N–methyl–D–aspartate (NMDA) and non–NMDA and non–NMDA receptor antagonists block the hyperexcitability of dorsal horn neurons during development of acute arthritis in rat's knee joint," *J. Neurosci.,* Oct. 1993, 70(4), 1365–1377.

Pershing, L.K., et al., "In vivo pharmacokinetics and pharmacodynamcis of topical Ketoconazole and miconazole in human stratum corneum," *Antimicrob. Agents Chemother,* Jan. 1994, 38(1), 90–95.

Przewlocki, R., et al., "Gene expression and localization of opioid peptides in immune cells of inflamed tissue; functional role in antinociception," *Neuroscience,* 1992, 48(2), 491–500.

Ramabadran, K., et al., "A critical analysis of the experimental evaluation of nociceptive reactions in animals," *Pharm. Res.,* 1986, 3(5), 263–270.

Randall, L.O., et al., "A method for measurement of analgesic activity on inflamed tissue," *Arch. Int. Pharmacodyn.,* 1957, CXI(4), 409–419.

Raynor, K., et al., "Pharmacological characterization of the cloned κ–, δ–, and μ–opioid receptors," *Mol. Pharmacol.,* 1994, 45, 330–334.

Remington's Pharmaceutical Sciences, *Mack Publishing co., Easton, PA,* 1980.

Roy, S.D., et al., "Transdermal delivery of narcotic analgesics: pH, anatomical, and subject influences cutaneous permeability of fentanyl and sufentanil," *Pharm. Res.,* 1990, 7(8), 842–847.

Sato, A., et al., "Changes in blood pressure and heart rate induced by movements of normal and inflamed knee joints," *Neurosci. Lett.,* 1984, 52, 55–60.

Schaible, H–G., et al., "Effects of an experimental arthritis on the sensory properties of fine articular afferent units," *J. of Neurophysiol.,* Nov. 1995, 54(5), 1109–1122.

Schaible, H–G., et al., "Afferent and spinal mechanisms of joint pain," *Pain,* 1993, 55, 5–54.

Simon, E.J., "Opioid receptors and endogenous opioid peptides," *Med. Res. Rev.,* 1991, 11(4), 357–374.

Stein, C., et al., "Peripheral opioid receptors mediating antinociception in inflammation. Evidence for involvement of Mu, Delta and Kappa receptors," *J. of Pharmacol. Exp. Ther.,* 1989, 248(3), 1269–1275.

Taber, R.I., et al., "Agonist and antagonist interactions of opioids on acetic acid–induced abdominal stretching in mice," *J. of Pharmacol. Exp. Ther.,* 1969, 169(1), 29–38.

Tjpølsen, A., et al., "The formalin test: an evaluation of the method," *Pain,* 1992, 51, 5–17.

Wheeler–Aceto H., et al., "Standardization of the rat paw formalin test for the evaluation of analgesics," *Psychopharmacology,* 1991, 104, 35–44.

Williamson, J.W., et al., "Reflex increase in blood pressure induced by leg compression in man," *J. of Physiol.,* 1994, 475.2, 351–357.

Wood, P.L., "Multiple opiate receptors: Support for unique mu, delta and kappa sites," *Neuropharmacology,* 1982, 21, 487–497.

LACTAM DERIVATIVES AND METHODS OF THEIR USE

FIELD OF THE INVENTION

The invention relates to lactam derivatives, pharmaceutical compositions containing these compounds, and methods for their pharmaceutical use. In certain embodiments, the lactam derivatives are agonists of the kappa opioid receptor and are useful, inter alia, for treating and/or preventing pain, pruritus, and gastrointestinal disorders.

BACKGROUND OF THE INVENTION

Opium and its derivatives are potent analgesics that also have other pharmacological effects, and exert their effects by interacting with high-affinity receptors. It has been shown by investigators that there are at least three major opioid receptor types in the central nervous system (hereinafter CNS) and in the periphery. These receptors, known as mu ($\mu$), delta ($\delta$) and kappa ($\kappa$), have distinct pharmacological profiles, anatomical distributions and functions. See, for example: Wood, P. L., *Neuropharmacology*, 21, 487–497, 1982; Simon, E. J., *Med. Res. Rev.*, 11, 357–374, 1991; Lutz et al., *J. Recept. Res.* 12, 267–286; and Mansour et al., Opioid I, ed. Herz, A. (Springer, Berlin) pp. 79–106, 1993. The $\delta$ receptors are abundant in CNS and mediate analgesia, gastrointestinal motility and various hormonal functions. The $\mu$ receptors bind morphine-like drugs and mediate the opiate phenomena associated with morphine, including analgesia, opiate dependence, cardiovascular and respiratory functions, and several neuroendocrine effects. The $\kappa$ receptors have a wide distribution in CNS and mediate a spectrum of functions including the modulation of drinking, water balance, food intake, tussis, gut motility, temperature control and various endocrine functions. They also produce analgesia. See, for example: Leander et al., *J. Pharmacol. Exp. Ther.* 234, 463–469, 1985; Morley et al., *Peptides* 4, 797–800, 1983; Manzanares et al., *Neuroendocrinology* 52, 200–205, 1990; and Iyengar et al., *J. Pharmacol. Exp. Ther,* 238, 429–436, 1986; U.S. Pat. No. 6,177,438 B1.

Most clinically used opioid analgesics, such as morphine and codeine, act as $\mu$ receptor agonists. These opioids have well-known, undesirable and potentially dangerous dependence forming side effects. Compounds that are $\kappa$-receptor agonists act as analgesics through interaction with $\kappa$ opioid receptors. The advantage of these agonists over the classical $\mu$ receptor agonists, such as morphine, lies in their ability to cause analgesia while being devoid of morphine-like behavioral effects and addiction liability.

A large number of classes of compounds which act as agonists at $\kappa$ opioid receptors have been described in the art including the following illustrative classes of compounds:

U.S. Pat. No. 4,065,573 discloses 4-amino-4-phenylcyclohexane ketal compounds allegedly having analgesic activity.

U.S. Pat. No. 4,145,435 discloses N-(2-aminocycloaliphatic)-phenylacetamide compounds allegedly having analgesic activity and narcotic antagonist activity.

U.S. Pat. No. 4,098,904 discloses N-(2-aminocycloaliphatic)-benzoamides and naphthamides allegedly useful for relieving pain.

U.S. Pat. No. 4,212,878 discloses phenylacetamide derivatives allegedly having analgesic properties and reduced physical dependence liability properties, relative to morphine and methadone.

U.S. Pat. No. 4,359,476 discloses substituted cycloalkane-amides allegedly useful as analgesic and having low abuse liability.

U.S. Pat. No. 4,438,130 discloses 1-oxa-, aza- and thia-spirocyclic compounds allegedly having analgesic activity, low physical dependence and abuse liability properties and little dysphoric inducing properties.

U.S. Pat. No. 4,663,343 discloses substituted naphthalenyloxy-1,2-diaminocyclohexyl amides allegedly useful as analgesics.

U.S. Pat. No. 4,906,655 discloses 1,2-cyclohexylaminoaryl amides allegedly having high kappa-opioid affinity, selectivity and potency and allegedly useful as analgesics, diuretics, anti-inflammatory and psychotherapeutic agents.

U.S. Pat. No. 5,532,266 discloses arylacetamides allegedly having high kappa-opioid affinity useful as pharmaceutical agents for providing an analgesic effect and/or neuroprotective effect.

U.S. Pat. No. 5,688,955 discloses substituted piperidines, substituted naphthalenes, aryl-substituted amides, and cyclohexyl-substituted amides having kappa opioid agonist activity, compositions containing them and methods of using them as analgesics.

U.S. Pat. No. 5,804,595 discloses amino acid conjugates of substituted 2-phenyl-N-[1-(phenyl)-2-(1-heterocycloalkyl- or heterocycloaryl-)ethyl]acetamides allegedly useful for selectively agonizing kappa opioid receptors in mammalian tissue.

There is still an unfulfilled need for compounds with kappa opioid receptor activity that may be used in methods to provide beneficial pharmaceutical characteristics while minimizing undesirable side effects generally associated with administering exogenous opioids. The present invention is directed to these, as well as other important ends.

SUMMARY OF THE INVENTION

The present invention is generally directed to lactam derivatives, pharmaceutical compositions containing these compounds, and methods for their pharmaceutical use.

In one embodiment, the invention is directed to compounds of formula I:

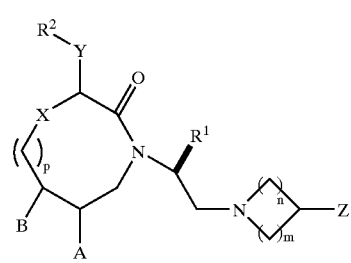

I wherein:
A and B are each H, or when taken together with the carbon atoms to which they are attached, form a carbon—carbon double bond;
X is —O— or a single bond;
Y is —O—, —CH$_2$—, or a single bond, provided that when X is —O—, Y cannot be —O—;
Z is —H or —OH;
R$^1$ is alkyl, aralkyl, or aryl;
R$^2$ is alkyl, aryl, or —NR$^3$R$^4$, provided that when Y is —O—, R$^2$ cannot be —NR$^3$R$^4$;

m and n are each independently an integer from 1 to 4, and the sum of (m+n) is an integer from 2 to 5;

p is the integer 1 or 2;

$R^3$ is H or alkyl;

$R^4$ is —C(=O)$R^5$, —C(=O)N$R^5R^6$, —SO$_2R^5$, —C(=O)NH$R^6$, aryl, or heteroaryl;

$R^5$ is alkyl, cycloalkyl, heterocycloalkyl, aralkyl, aryl, or heteroaryl; and $R^6$ is H, alkyl, aryl, aralkyl, or together with the nitrogen atom to which they are attached, $R^5$ and $R^6$ form a 4–8 membered heterocycloalkyl ring, said heterocycloalkyl ring optionally interrupted by one or more additional heteroatoms selected from nitrogen, oxygen, and sulfur;

or a stereoisomer, prodrug, pharmaceutically acceptable salt, hydrate, solvate, acid salt hydrate, N-oxide or isomorphic crystalline form thereof.

In another embodiment, the invention is directed to pharmaceutical compositions comprising a pharmaceutically acceptable carrier and an effective amount of a compound of formula I. In certain preferred embodiments, the pharmaceutical compositions may further comprise an opioid and/or another active ingredient selected from the group consisting of antibiotics, antivirals, antifungals, anti-inflammatories, anesthetics and mixtures thereof.

In another embodiment, the invention is directed to compounds of formula II:

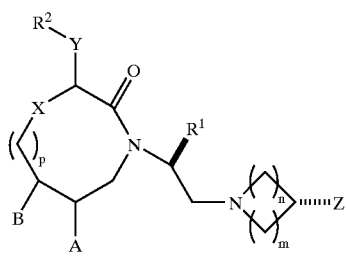

II and pharmaceutical compositions comprising a pharmaceutically acceptable carrier and an effective amount of a compound of formula II.

In another embodiment, the invention is directed to compounds of formula III:

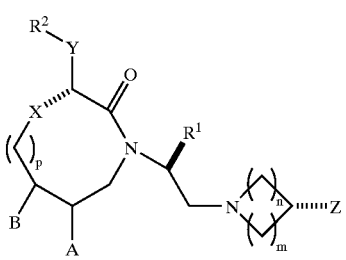

III and pharmaceutical compositions comprising a pharmaceutically acceptable carrier and an effective amount of a compound of formula III.

In another embodiment, the invention is directed to compounds of formula IV:

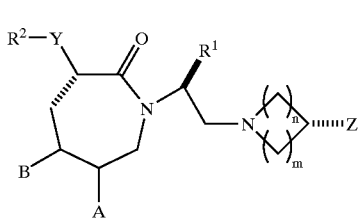

IV and pharmaceutical compositions comprising a pharmaceutically acceptable carrier and an effective amount of a compound of formula IV.

In another embodiment, the invention is directed to compounds of formula V:

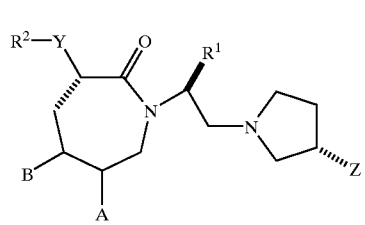

V and pharmaceutical compositions comprising a pharmaceutically acceptable carrier and an effective amount of a compound of formula V.

In another embodiment, the invention is directed to compounds of formula VI:

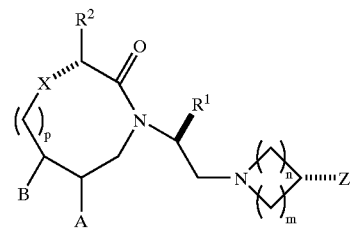

VI and pharmaceutical compositions comprising a pharmaceutically acceptable carrier and an effective amount of a compound of formula VI.

In another embodiment, the invention is directed to compounds of formula VII:

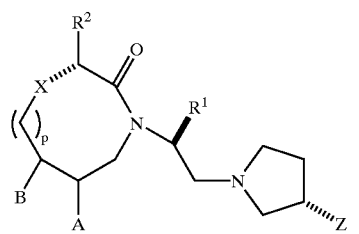

VII and pharmaceutical compositions comprising a pharmaceutically acceptable carrier and an effective amount of a compound of formula VII.

In another embodiment, the invention is directed to compounds of formula VIII:

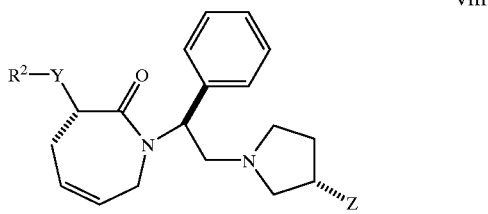

VIII and pharmaceutical compositions comprising a pharmaceutically acceptable carrier and an effective amount of a compound of formula VIII.

In another embodiment, the invention is directed to compounds of formula IX:

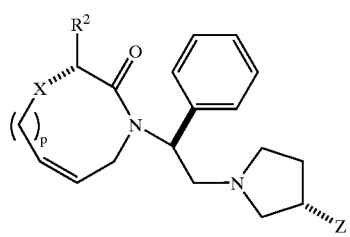

IX and pharmaceutical compositions comprising a pharmaceutically acceptable carrier and an effective amount of a compound of formula IX.

In another embodiment, the invention is directed to methods of binding opioid receptors, including κ opioid receptors, in a patient in need thereof, comprising the step of administering to the patient an effective amount of a compound of formula I.

In yet another embodiment, the invention is directed to methods for preventing or treating gastrointestinal dysfunction comprising the step of administering to a patient in need thereof, a composition comprising an effective amount of a compound of formula I.

In other embodiments, the invention is directed to methods for preventing or treating ileus comprising the step of administering to a patient in need thereof, a composition comprising an effective amount of a compound of formula I.

In another embodiment, the invention is directed to methods for preventing or treating pain comprising the step of administering to a patient in need thereof, a composition comprising an effective amount of an opioid and an effective amount of a compound of formula I.

In another embodiment, the invention is directed to methods for preventing or treating pruritic dermatoses and conditions characterized by pruritic dermatosis as a symptom, including allergic dermatitis, atopy, contact dermatitis, psoriasis, eczema, opioid-induced pruritus, and insect bites, comprising the step of administering to a patient in need thereof, a composition comprising an effective amount of a compound of formula I.

In another embodiment, the invention is directed to methods for preventing or treating cerebral edema, comprising the step of administering to a patient in need thereof, a composition comprising an effective amount of a compound of formula I.

In other embodiments, the invention is directed to methods for preventing or treating oxygen supply deficiency of the central nervous system, comprising the step of administering to a patient in need thereof, a composition comprising an effective amount of a compound of formula I.

In another embodiment, the invention is directed to methods for inducing diuresis, comprising the step of administering to a patient in need thereof, a composition comprising an effective amount of a compound of formula I.

In yet another embodiment, the invention is directed to methods for preventing or treating tussis, comprising the step of administering to a patient in need thereof, a composition comprising an effective amount of a compound of formula I.

DESCRIPTION OF ILLUSTRATIVE EMBODIMENTS

As employed above and throughout the disclosure, the following terms, unless otherwise indicated, shall be understood to have the following meanings.

As used herein, "alkyl" refers to an optionally substituted, saturated straight, branched, or cyclic hydrocarbon having from about 1 to about 20 carbon atoms (and all combinations and subcombinations of ranges and specific numbers of carbon atoms therein), with from about 1 to about 8 carbon atoms, herein referred to as "lower alkyl", being preferred. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl.

As used herein, "alkenyl" refers to an alkyl group of at least 2 carbon atoms having one or more double bonds, wherein alkyl is as previously defined. Alkenyl groups can be optionally substituted.

As used herein, "aryl" refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

As used herein, "perhaloalkyl" refers to an alkyl group, wherein all of the hydrogens are replaced by halo (F, Cl, Br, I) atoms, and alkyl is as previously defined.

As used herein, "aralkyl" refers to alkyl radicals bearing an aryl substituent and having from about 6 to about 50 carbon atoms (and all combinations and subcombinations of ranges and specific numbers of carbon atoms therein), with from about 6 to about 10 carbon atoms being preferred. Aralkyl groups can be optionally substituted. Non-limiting examples include, for example, benzyl, diphenylmethyl, triphenylmethyl, phenylethyl, and diphenylethyl.

As used herein, "heteroaryl" refers to an optionally substituted, mono-, di-, tri-, or other multicyclic aromatic ring system that includes at least one, and preferably from 1 to about 4 sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples of heteroaryl groups include, for example, pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl.

As used herein, "cycloalkyl" refers to an optionally substituted, alkyl group having one or more rings in their structures and having from about 3 to about 20 carbon atoms and all combinations and subcombinations of ranges and specific numbers of carbon atoms therein), with from about 3 to about 10 carbon atoms being preferred. Multi-ring structures may be bridged or fused ring structures. Groups include, but are not limited to, cyclopropyl, cyclobutyl, cyclopentyl, cyclohexyl, cyclooctyl, and adamantyl.

As used herein, "alkylcycloalkyl" refers to an optionally substituted ring system comprising a cycloalkyl group having one or more alkyl substituents. Exemplary alkylcycloalkyl groups include 2-methylcyclohexyl, 3,3-dimethylcyclopentyl, trans-2,3-dimethylcyclooctyl, and 4-methyldecahydronaphthalenyl.

As used herein, "heteroaralkyl" refers to an optionally substituted, heteroaryl substituted alkyl radicals having from about 2 to about 50 carbon atoms (and all combinations and subcombinations of ranges and specific numbers of carbon atoms therein), with from about 6 to about 25 carbon atoms being preferred. Non-limiting examples include 2-(1H-pyrrol-3-yl)ethyl, 3-pyridylmethyl, 5-(2H-tetrazolyl)methyl, and 3-(pyrimidin-2-yl)-2-methylcyclopentanyl.

As used herein, "heterocycloalkyl" refers to an optionally substituted, mono-, di-, tri-, or other multicyclic aliphatic ring system that includes at least one, and preferably from 1 to about 4 sulfur, oxygen, or nitrogen heteroatom ring members. Heterocycloalkyl groups can have from about 3 to about 20 carbon atoms (and all combinations and subcombinations of ranges and specific numbers of carbon atoms therein), with from about 4 to about 10 carbons being preferred. The heterocycloalkyl group may be unsaturated, and may also be fused to aromatic rings. Examples of heterocycloalkyl groups include, for example, tetrahydrofuranyl, tetrahydrothienyl, piperidinyl, pyrrolidinyl, isoxazolidinyl, isothiazolidinyl, pyrazolidinyl, oxazolidinyl, thiazolidinyl, piperazinyl, morpholinyl, piperadinyl, decahydroquinolyl, octahydrochromenyl, octahydro-cyclopenta[c]pyranyl, 1,2,3,4,-tetrahydroquinolyl, octahydro-[2]pyrindinyl, decahydrocycloocta[c]furanyl, and imidazolidinyl.

As used herein, the term "spiroalkyl" refers to an optionally substituted, alkylene diradical, both ends of which are bonded to the same carbon atom of the parent group to form a spirocyclic group. The spiroalkyl group, taken together with its parent group, as herein defined, has 3 to 20 ring atoms. Preferably, it has 3 to 10 ring atoms. Non-limiting examples of a spiroalkyl group taken together with its parent group include 1-(1-methyl-cyclopropyl)-propan-2-one, 2-(1-phenoxy-cyclopropyl)-ethylamine, and 1-methyl-spiro[4.7]dodecane.

As used herein, "alkoxy" and "alkoxyl" refer to an optionally substituted alkyl-O-group wherein alkyl is as previously defined. Exemplary alkoxy and alkoxyl groups include methoxy, ethoxy, n-propoxy, i-propoxy, n-butoxy, and heptoxy.

As used herein, "aryloxy" and "aryloxyl" refer to an optionally substituted aryl-O-group wherein aryl is as previously defined. Exemplary aryloxy and aryloxyl groups include phenoxy and naphthoxy.

As used herein, "aralkoxy" and "aralkoxyl" refer to an optionally substituted aralkyl-O-group wherein aralkyl is as previously defined. Exemplary aralkoxy and aralkoxyl groups include benzyloxy, 1-phenylethoxy, 2-phenylethoxy, and 3-naphthylheptoxy.

Typically, substituted chemical moieties include one or more substituents that replace hydrogen. Exemplary substituents include, for example, halo (e.g, F, Cl, Br, I), alkyl, cycloalkyl, alkylcycloalkyl, alkenyl, alkynyl, aralkyl, aryl, heteroaryl, heteroaralkyl, spiroalkyl, heterocycloalkyl, hydroxyl (—OH), alkoxyl, aryloxyl, aralkoxyl, nitro (—NO2), cyano (—CN), amino (—NH$_2$), -N-substituted amino (—NHR"), -N,N-disubstituted amino (—N(R")R"), carboxyl (—COOH), —C(=O)R", —OR", —C(=O)OR", —NHC(=O)R", aminocarbonyl (—C(=O)NH$_2$), -N-substituted aminocarbonyl (—C(=O)NHR"), -N,N-disubstituted aminocarbonyl (—C(=O)N(R")R"), thiol, thiolato (SR"), sulfonic acid (SO$_3$H), phosphonic acid (PO$_3$H), S(=O)$_2$R", S(=O)$_2$NH$_2$, S(=O)$_2$NHR", S(=O)$_2$NR"R", NHS(=O)$_2$R", N—R"S(=O)$_2$R", CF$_3$, CF$_2$CF$_3$, NHC(=O)NHR", NHC(=O)NR"R", NR"C(=O)NHR", NR"C(=O)NR"R", NR"C(=O)R" and the like. In relation to the aforementioned substituents, each moiety R" can be, independently, any of H, alkyl, cycloalkyl, alkenyl, aryl, aralkyl, heteroaryl, or heterocycloalkyl, for example.

As used herein, "opioid" refers to all agonist and antagonists with morphine-like activity as well as to naturally occurring and synthetic opioid peptides. Non-limiting examples of compounds with morphine-like activity include the family of drugs derived from opium, such as for example, morphine and codeine, thebaine, and a wide variety of semi synthetic related compounds derived therefrom.

As used herein, "analgesic" refers to pharmaceutical compounds that have the ability to reduce or eliminate pain and/or the perception of pain without a loss of consciousness.

As used herein, "effective amount" refers to an amount of a compound as described herein that may be therapeutically effective to inhibit, prevent or treat the symptoms of particular disease, disorder, condition, or side effect. Such diseases, disorders, conditions, and side effects include, but are not limited to, those pathological conditions associated with the administration of opioids (for example, in connection with the treatment and/or prevention of pain), wherein the treatment or prevention comprises, for example, inhibiting the activity thereof by contacting cells, tissues or receptors with compounds of the present invention. Thus, for example, the term "effective amount", when used in connection with opioids, or opioid replacements, for example, for the treatment of pain, refers to the treatment and/or prevention of the painful condition. The term "effective amount", when used in connection with anti-pruritic compounds, refers to the treatment and/or prevention of symptoms, diseases, disorders, and conditions typically associated with pruritus and other related dermatoses. The term "effective amount", when used in connection with compounds active against gastrointestinal dysfunction, refers to the treatment and/or prevention of symptoms, diseases, disorders, and conditions typically associated with gastrointestinal dysfunction. The term "effective amount", when used in connection with anti-ileus compounds, refers to the treatment and/or prevention of symptoms, diseases, disorders, and conditions typically associated with ileus. The term "effective amount", when used in connection with compounds useful in the treatment and/or prevention of cerebral edema, refers to the treatment and/or prevention of symptoms, diseases, disorders, and conditions typically associated with cerebral edema and other related conditions. The term "effective amount", when used in connection with anti-hypoxia compounds, refers to the treatment and/or prevention of symptoms, diseases, disorders, and conditions typically associated with hypoxia, such as oxygen supply deficiency to the central nervous system. The term "effective amount", when used in connection with anti-tussive compounds, refers to the treatment and/or prevention of tussis. The term "effective amount", when used in connection with diuretic compounds, refers to the inducement of diuresis.

As used herein, "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, "in combination with", "combination therapy" and "combination products" refer, in certain embodiments, to the concurrent administration to a patient of opioids and the compounds of formula (I). When administered in combination, each component may be administered at the same time or sequentially in any order at different points in time. Thus, each component may be administered separately but sufficiently closely in time so as to provide the desired therapeutic effect.

As used herein, "dosage unit" refers to physically discrete units suited as unitary dosages for the particular individual to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound (s).

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxyl groups often exist in equilibrium with their zwitterionic forms. Thus, any of the compounds described herein throughout that contain, for example, both amino and carboxyl groups, also include reference to their corresponding zwitterions.

As used herein, "patient" refers to animals, including mammals, preferably humans.

As used herein, "stereoisomers" refers to compounds that have identical chemical constitution, but differ as regards the arrangement of the atoms or groups in space.

As used herein, "N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

As used herein, "gastrointestinal dysfunction" refers collectively to maladies of the stomach, small and large intestine. Non-limiting examples of gastrointestinal dysfunction include, for example, irritable bowel syndrome, opioid-bowel dysfunction, post-operative ileus, opioid-induced ileus, colitis, post-operative emesis, opioid-induced emesis, decreased gastric motility, decreased gastric emptying, inhibition of small intestinal propulsion, inhibition of large intestinal propulsion, increased amplitude of non-propulsive segmental contractions, constriction of sphincter of Oddi, increased anal sphincter tone, impaired reflex relaxation with rectal distension, diminished gastric, biliary, pancreatic or intestinal secretions, increased absorption of water from bowel contents, gastro-esophageal reflux, gastroparesis, cramping, bloating, abdominal or epigastric pain and discomfort, constipation, or delayed absorption of orally administered medications or nutritive substances.

As used herein, "pain" refers to the perception or condition of unpleasant sensory or emotional experience, associated with actual or potential tissue damage or described in terms of such damage. "Pain" includes, but is not limited to, two broad categories of pain: acute and chronic pain (Buschmann, H.; Christoph, T; Friderichs, E.; Maul, C.; Sundermann, B; eds. *Analgesics*, Wiley-VCH, Verlag GMbH & Co. KgaA, Weinheim; 2002; Jain, K. K. "A Guide to Drug Evaluation For Chronic Pain"; *Emerging Drugs*, 5(2), 241–257(2000)). Non-limiting examples of pain include nociceptive pain, inflammatory pain, visceral pain, somatic pain, neuropathic pain, AIDS pain, cancer pain, phantom pain, and psychogenic pain, and pain resulting from hyperalgesia, allodynia and the like.

As used herein, "pruritus" refers to a symptom of a disease, disorder, or condition which is manifested by itching, that is, an uncomfortable sensation due to irritation of a peripheral sensory nerve.

As used herein, "tussis" refers to a coughing condition, and "antitussive" agents refer to those materials that modulate the coughing response.

As used herein, "diuretic" refers to an agent that modulates the water balance in a patient.

As used herein, "pruritic dermatosis" refers to any skin diseases, disorders, or conditions of which itching is a symptom. Non-limiting examples include allergic dermatitis, atopy, contact dermatitis, psoriasis, eczema, opioid-induced pruritus, uremic pruritus, and insect bites.

When any variable occurs more than one time in any constituent or in any formula, its definition in each occurrence is independent of its definition at every other occurrence. Combinations of substituents and/or variables are permissible only if such combinations result in stable compounds.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form or to any specific optical; or geometric isomer, except where such stereochemistry is clearly defined.

Accordingly, in one embodiment, the invention provides novel pharmaceutically active compounds of formula I:

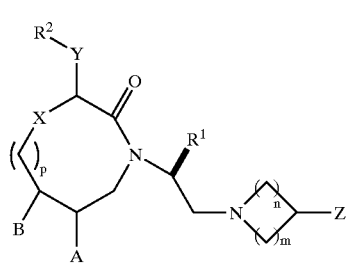

I wherein:
A and B are each H, or when taken together with the carbon atoms to which they are attached, form a carbon—carbon double bond;
X is —O— or a single bond;
Y is —O—, —CH$_2$—, or a single bond, provided that when X is —O—, Y cannot be —O—;
Z is H or —OH;
R$^1$ is alkyl, aralkyl, or aryl;
R$^2$ is alkyl, aryl, or —NR$^3$R$^4$, provided that when Y is —O—, R$^2$ cannot be —NR$^3$R$^4$;
m and n are each independently an integer from 1 to 4, and the sum of (m+n) is an integer from 2 to 5;
p is the integer 1 or 2;
R$^3$ is H or alkyl;
R$^4$ is —C(=O)R$^5$, —C(=O)NR$^5$R$^6$, —SO$_2$R$^5$, —C(=O)NHR$^6$, aryl, or heteroaryl;
R$^5$ is alkyl, cycloalkyl, heterocycloalkyl, aralkyl, aryl, or heteroaryl; and
R$^6$ is H, alkyl, aryl, aralkyl, or together with the nitrogen atom to which they are attached, R$^5$ and R$^6$ form a 4–8 membered heterocycloalkyl ring, said heterocycloalkyl ring optionally interrupted by one or more additional heteroatoms selected from nitrogen, oxygen, and sulfur;
or a stereoisomer, prodrug, pharmaceutically acceptable salt, hydrate, solvate, acid salt hydrate, N-oxide or isomorphic crystalline form thereof.

In certain preferred embodiments, A and B form a carbon—carbon double bond.

In certain preferred embodiments, X is a single bond.

In certain preferred embodiments, Y is —O— or a single bond. More preferably, Y is a single bond. In certain alternative embodiments when Y is a single bond, X is —O—. Preferably, in these alternative embodiments, R$^2$ is aryl. More preferably, in these alternative embodiments, R$^2$ is aryl and p is the integer 2.

In certain preferred embodiments, Z is H.

In certain preferred embodiments, R$^1$ is aryl. More preferably, R$^1$ is phenyl.

In certain preferred embodiments, R$^2$ is aryl. More preferably, when R$^2$ is aryl, the aryl is substituted with at least one of halo, alkoxy, mono- or perhaloalkyl, aryl, aryloxy, —NR'SO$_2$-alkyl, CH$_2$NR"SO$_2$-alkyl, or SO$_2$NR'R", wherein R' is H or alkyl and R" is alkyl or heterocycloalkyl, or together with the nitrogen atom to which they are attached, R' and R" form a 4- to 7-membered heterocycloalkyl ring. Even more preferably, R$^2$ is phenyl. Most preferably, when R$^2$ is phenyl, the phenyl is substituted with at least one of halo, alkoxy, mono- or perhaloalkyl, aryl, aryloxy, —NR'SO$_2$-alkyl, CH$_2$NR'SO$_2$-alkyl, or SO$_2$NR'R", wherein R' is H or alkyl and R" is alkyl or heterocycloalkyl, or together with the nitrogen atom to which they are attached, R' and R" form a 4- to 7-membered heterocycloalkyl ring.

In certain preferred embodiments, m and n are each independently an integer from 1 to 2, and the sum of (m+n) is the integer 3. More preferably, m is the integer 1 and n is the integer 2.

In certain preferred embodiments, p is the integer 1. More preferably, when p is the integer 1, X is a single bond.

In certain preferred embodiments of the present invention, the compounds of formula I have the structure corresponding to formula II:

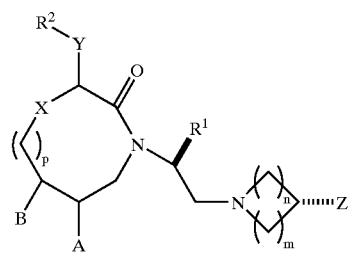

II wherein A, B, X, Y, Z, R$^1$, R$^2$, m, n, and p are as set forth above.

More preferably, the formula I compounds have the structure corresponding to formula III:

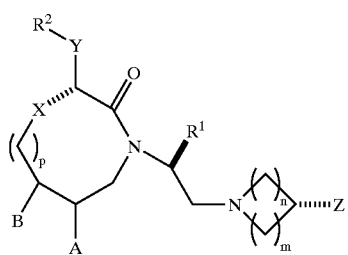

III wherein A, B, X, Y, Z, R$^1$, R$^2$, m, n, and p are as set forth above even more preferably, these compounds of formula I have formula IV:

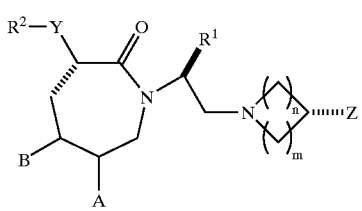

IV wherein A, B, X, Y, Z, R$^1$, R$^2$ are as set forth above.

Even more preferably, compounds of formula I have formula V:

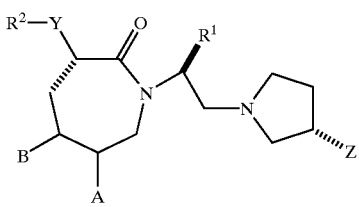

V wherein A, B, Y, Z, $R^1$ and $R^2$ are as set forth above.

Yet even more preferably, these compounds of formula I have the formula VIII:

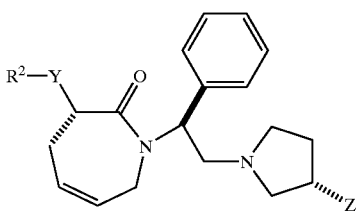

VIII wherein Y, Z and $R^2$ are as set forth above.

In certain preferred alternative embodiments, the compounds of formula I have the formula VI:

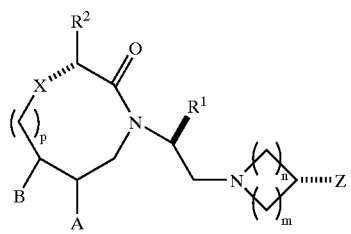

VI wherein A, B, X, Z, $R^1$, $R^2$, m, n, and p are as set forth above.

In other more preferred alternative embodiments, the compounds of formula I have the formula VII:

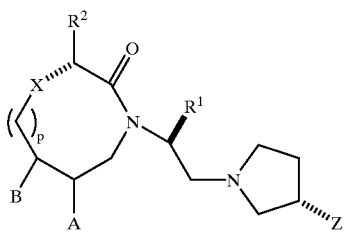

VII wherein A, B, X, Z, $R^1$, $R^2$, and p are as set forth above.

In other yet even more preferred alternative embodiments, the compounds of formula I have the formula IX:

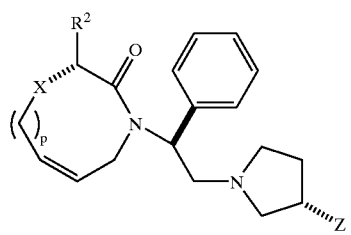

IX wherein X, Z, $R^2$ and p are as set forth above.

In any of the above teachings, a compound of the invention may be either a compound of the formula herein described, or a stereoisomer, prodrug, pharmaceutically acceptable salt, hydrate, solvate, acid salt hydrate, N-oxide or isomorphic crystalline form thereof.

The compounds employed in the methods of the present invention may exist in prodrug form. As used herein, "prodrug" is intended to include any covalently bonded carriers which release the active parent drug, for example, as according to formula I or other formulas or compounds employed in the methods of the present invention in vivo when such prodrug is administered to a mammalian subject. Since prodrugs are known to enhance numerous desirable qualities of pharmaceuticals (e.g., solubility, bioavailability, manufacturing, etc.) the compounds employed in the present methods may, if desired, be delivered in prodrug form. Thus, the present invention contemplates methods of delivering prodrugs. Prodrugs of the compounds employed in the present invention, for example formula I, may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

The compounds employed in the methods of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

Compounds employed in the present methods may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl group and the tert-butyloxycarbonyl group. Other preferred protecting groups that may be employed in accordance with the present invention may be described in Greene, T. W. and Wuts, P. G. M., *Protective Groups in Organic Synthesis* 2d. Ed., Wiley & Sons, 1991.

The kappa agonist compounds employed in the methods of the present invention may be administered by any means that results in the contact of the active agent with the agent's site of action in the body of a patient. The compounds may be administered by any conventional means available for use in conjunction with pharmaceuticals, either as individual therapeutic agents or in a combination of therapeutic agents. For example, they may be administered as the sole active agent in a pharmaceutical composition, or they can be used in combination with other therapeutically active ingredients including, for example, opioid analgesic agents. In such combinations, selected compounds of the invention may provide equivalent or even enhanced therapeutic activity such as, for example, pain ameliorization, while providing reduced adverse side effects associated with opioids, such as addiction or pruritus, by lowering the amount of opioid required to achieve a therapeutic effect.

The compounds are preferably combined with a pharmaceutical carrier selected on the basis of the chosen route of administration and standard pharmaceutical practice as described, for example, in *Remington's Pharmaceutical Sciences* (Mack Publishing Co., Easton, Pa., 1980), the disclosures of which are hereby incorporated herein by reference, in their entirety.

In addition to the pharmaceutical carrier, the compounds of formula I may be co-administered with at least one opioid. Suitable opioids include alfentanil, buprenorphine, butorphanol, codeine, dezocine, dihydrocodeine, fentanyl, hydrocodone, hydromorphone, levorphanol, meperidine (pethidine), methadone, morphine, nalbuphine, oxycodone, oxymorphone, pentazocine, propiram, propoxyphene, sufentanil, tramadol and mixtures thereof.

Compounds of the present invention can be administered to a mammalian host in a variety of forms adapted to the chosen route of administration, e.g., orally or parenterally. Parenteral administration in this respect includes administration by the following routes: intravenous, intramuscular, subcutaneous, rectal, intraocular, intrasynovial, transepithelial including transdermal, ophthalmic, sublingual and buccal; topically including ophthalmic, dermal, ocular, rectal, and nasal inhalation via insufflation aerosol.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should preferably contain at least 0.1% of active compound. The percentage of the compositions and preparations may, of course, be varied and may conveniently be, for example, from about 2 to about 6% of the weight of the unit. The amount of active compound in such therapeutically useful compositions is preferably such that a suitable dosage will be obtained. Preferred compositions or preparations according to the present invention may be prepared so that an oral dosage unit form contains from about 0.1 to about 1000 mg of active compound.

The tablets, troches, pills, capsules and the like may also contain one or more of the following: a binder, such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent such as sucrose, lactose or saccharin; or a flavoring agent, such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. Of course, any material used in preparing any dosage unit form is preferably pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or a pharmacologically acceptable salt can be prepared in water suitably mixed with a surfactant, such as hydroxypropylcellulose. A dispersion can also be prepared in glycerol, liquid polyethylene glycols and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compound in the required amount, in the appropriate solvent, with various of the other ingredients enumerated above, as required, followed by filtered sterilization. Generally, dispersions may be prepared by incorporating the sterilized active ingredient into a sterile vehicle that contains the basic dispersion medium and the required other ingredients from those enumerated above. In the case of sterile powders for the preparation of sterile injectable solutions, the preferred methods of preparation may include vacuum drying and the freeze drying technique which yield a powder of the active ingredient, plus any additional desired ingredient from the previously sterile-filtered solution thereof.

The therapeutic compounds of this invention may be administered to a patient alone or in combination with a pharmaceutically acceptable carrier. As noted above, the relative proportions of active ingredient and carrier may be determined, for example, by the solubility and chemical nature of the compound, chosen route of administration and standard pharmaceutical practice.

The dosage of the compounds of the present invention that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. The therapeutic human dosage, based on physiological studies using rats, may generally range from about 0.01 mg to about 100 mg/kg of body weight per day, and all combinations and subcombinations of ranges therein. Alternatively, the therapeutic human dosage may be from about 0.4 mg to about 10 g or higher, and may be administered in several different dosage units from once to several times a day. Generally speaking, oral administration may require higher dosages.

The compounds of the invention may also be formulated with other optional active ingredients, in addition to the optional opioids, and in addition to the optional pharmaceutical-acceptable carriers. Other active ingredients include, but are not limited to, antibiotics, antivirals, antifungals, anti-inflammatories, including steroidal and non-steroidal anti-inflammatories, anesthetics and mixtures thereof. Such additional ingredients include any of the following.

a. Antibacterial agents

Aminoglycosides, such as Amikacin, Apramycin, Arbekacin, Bambermycins, Butirosin, Dibekacin, Dihydrostreptomycin, Fortimicin(s), Fradiomycin, Gentamicin, Ispamicin, Kanamycin, Micronomicin, Neomycin, Neomycin Undecylenate, Netilmicin, Paromomycin, Ribostamycin, Sisomicin, Spectinomycin, Streptomycin, Streptonicozid and Tobramycin;

Amphenicols, such as Azidamfenicol, Chloramphenicol, Chloramphenicol Palmirate, Chloramphenicol Pantothenate, Florfenicol, Thiamphenicol;

Ansamycins, such as Rifamide, Rifampin, Rifamycin and Rifaximin; β-Lactams;

Carbapenems, such as Imipenem;

Cephalosporins, such as 1-Carba (dethia) Cephalosporin, Cefactor, Cefadroxil, Cefamandole, Cefatrizine, Cefazedone, Cefazolin, Cefixime, Cefinenoxime, Cefodizime, Cefonicid, Cefoperazone, Ceforanide, Cefotaxime, Cefotiam, Cefpimizole, Cefpirimide, Cefpodoxime Proxetil, Cefroxadine, Cefsulodin, Ceftazidime, Cefteram, Ceftezole, Ceflibuten, Ceftizoxime, Ceftriaxone, Cefuiroxime, Cefuzonam, Cephacetrile Sodium, Cephalexin, Cephaloglycin, Cephaloridine, Cephalosporin, Cephalothin, Cephapirin Sodium, Cephradine and Pivcefalexin;

Cephamycins such as Cefbuperazone, Cefmetazole, Cefminox, Cefetan and Cefoxitin;

Monobactams such as Aztreonam, Carumonam and Tigemonan;

Oxacephems such as Flomoxef and Moxolactam;

Penicillins such as Amidinocillin, Amdinocillin, Pivoxil, Amoxicillin, Ampicillan, Apalcillin, Aspoxicillin, Azidocillan, Azlocillan, Bacampicillin, Benzylpenicillinic Acid, Benzylpenicillin, Carbenicillin, Carfecillin, Carindacillin, Clometocillin, Cloxacillin, Cyclacillin, Dicloxacillin, Diphenicillin, Epicillin, Fenbenicillin, Floxicillin, Hetacillin, Lenampicillin, Metampicillin, Methicillin, Mezlocillin, Nafcillin, Oxacillin, Penamecillin, Penethamate Hydriodide, Penicillin G Benethamine, Penicillin G Benzathine, Penicillin G Benzhydrylamine, Penicillin G Calcium, Penicillin G Hydragamine, Penicillin G Potassium, Penicillin G Procaine, Penicillin N, Penicillin O, Penicillin V, Penicillin V Benzathine, Penicillin V Hydrabamine, Penimepicycline, Phenethicillin, Piperacillin, Pivapicillin, Propicillin, Quinacillin, Sulbenicillin, Talampicillin, Temocillin and Ticarcillin;

Lincosumides such as Clindamycin and Lincomycin;

Macrolides such as Azithromycin, Carbomycin, Clarithromycin, Erythromycin(s) and Derivatives, Josamycin, Leucomycins, Midecamycins, Miokamycin, Oleandomycin, Primycin, Rokitamycin, Rosaramicin, Roxithromycin, Spiramycin and Troleandomycin;

Polypeptides such as Amphomycin, Bacitracin, Capreomycin, Colistin, Enduracidin, Enviomycin, Fusafungine, Gramicidin(s), Gramicidin S, Mikamycin, Polymyxin, Polymyxin .beta.-Methanesulfonic Acid, Pristinamycin, Ristocetin, Teicoplanin, Thiostrepton, Tuberactinomycin, Tyrocidine, Tyrothricin, Vancomycin, Viomycin(s), Virginiamycin and Zinc Bacitracin;

Tetracyclines such as Spicycline, Chlortetracycline, Clomocycline, Demeclocycline, Doxycycline, Guamecycline, Lymecycline, Meclocycline, Methacycline, Minocycline, Oxytetracycline, Penimepicycline, Pipacycline, Rolitetracycline, Sancycline, Senociclin and Tetracycline; and others such as Cycloserine, Mupirocin, Tuberin.

b. Synthetic Antibacterials 2,4-Diaminopyrimidines such as Brodimoprim, Tetroxoprim and Trimethoprim;

Nitrofurans such as Furaltadone, Furazolium, Nifuradene, Nifuratel, Nifurfoline, Nifurpirinol, Nifurprazine, Nifurtoinol and Nitrofurantoin;

Quinolones and analogs thereof, such as Amifloxacin, Cinoxacin, Ciprofloxacin, Difloxacin, Enoxacin, Fleroxacin, Flumequine, Lomefloxacin, Miloxacin, Nalidixic Acid, Norfloxacin, Ofloxacin, Oxolinic Acid, Perfloxacin, Pipemidic Acid, Piromidic Acid, Rosoxacin, Temafloxacin and Tosufloxacin;

Sulfonamides such as Acetyl Sulfamethoxypyrazine, Acetyl Sulfisoxazole, Azosulfamide, Benzylsulfamide, Chloramine-.beta., Chloramine-T, Dichloramine-T, Formosulfathiazole, N.sup.2-Formyl-sulfisomidine, N.sup.4-.beta.-D-Glucosylsulfanilamide, Mafenide, 4'-(Methyl-sulfamoyl)sulfanilanilide, p-Nitrosulfathiazole, Noprylsulfamide, Phthalylsulfacetamide, Phthalylsulfathiazole, Salazosulfadimidine, Succinylsulfathiazole, Sulfabenzamide, Sulfacetamide, Sulfachlorpyridazine, Sulfachrysoidine, Sulfacytine, Sulfadiazine, Sulfadicramide, Sulfadimethoxine, Sulfadoxine, Sulfaethidole, Sulfaguanidine, Sulfaguanol, Sulfalene, Sulfaloxic Acid, Sulfamerazine, Sulfameter, Sulfamethazine, Sulfamethizole, Sulfamethomidine, Sulfamethoxazole, Sulfamethoxypyridazine, Sulfametrole, sulfamidochrysoidine, Sulfamoxole, Sulfanilamide, Sulfanilamidomethanesulfonic Acid Triethanolamine Salt, 4-Sulfanilamidosalicyclic Acid, N.sup.4-Sulfanilylsulfanilamide, Sulfanilylurea, N-Sulfanilyl-3,4-xylamide, Sulfanitran, Sulfaperine, Sulfaphenazole, Sulfaproxyline, Sulfapyrazine, Sulfapyridine, Sulfasomizole, Sulfasymazine, Sulfathiazole, Sulfathiourea, Sulfatolamide, Sulfisomidine and Sulfisoxazole;

Sulfones, such as Acedapsone, Acediasulfone, Acetosulfone, Dapsone, Diathymosulfone, Glucosulfone, Solasulfone, Succisulfone, Sulfanilic Acid, p-Sulfanilylbenzylamine, p,p'-sulfonyldianiline-N,N'digalactoside, Sulfoxone and Thiazolsulfone;

Others such as Clofoctol, Hexedine, Magainins, Methenamine, Methenamine Anhydromethylene-citrate, Methenamine Hippurate, Methenamine Mandelate, Methenamine Sulfosalicylate, Nitroxoline, Squalamine and Xibomol.

c. Antifungal (Antibiotics)

Polyenes such as Amphotericin-B, Candicidin, Dermostatin, Filipin, Fungichromin, Hachimycin, Hamycin, Lucensomycin, Mepartricin, Natamycin, Nystatin, Pecilocin, Perimycin; and others, such as Azaserine, Griseofulvin, Oligomycins, Pyrrolnitrin, Siccanin, Tubercidin and Viridin.

d. Antifungal (Synthetic)

Allylamines such as Naftifine and terbinafine;

Imidazoles such as Bifonazole, Butoconazole, Chlordantoin, Chlormidazole, Cloconazole, Clotrimazole, Econazole, Enilconazole, Finticonazole, Isoconazole, Ketoconazole, Miconazole, Omoconazole, Oxiconazole Nitrate, Sulconazole and Tioconazole;

Triazoles such as Fluconazole, Itraconazole, Terconazole;

Others such as Acrisorcin, Amorolfine, Biphenamine, Bromosalicylchloranilide, Buclosamide, Chlophenesin, Ciclopirox, Cloxyquin, Coparaffinate, Diamthazole, Dihydrochloride, Exalamide, Flucytosine, Halethazole, Hexetidine, Loflucarban, Nifuratel, Potassium Iodide, Propionic Acid, Pyrithione, Salicylanilide, Sulbentine, Tenonitrozole, Tolciclate, Tolindate, Tolnaftate, Tricetin, Ujothion, and Undecylenic Acid.

e. Antiglaucoma Agents

Antiglaucoma agents, such as Dapiprazoke, Dichlorphenamide, Dipivefrin and Pilocarpine.

f. Anti-Inflammatory Agents

Corticosteroids, aminoarylcarboxylic Acid Derivatives such as Etofenamate, Meclofenamic Acid, Mefanamic Acid, Niflumic Acid;

Arylacetic Acid Derivatives such as Acemetacin, Amfenac Cinmetacin, Clopirac, Diclofenac, Fenclofenac, Fenclorac, Fenclozic Acid, Fentiazac, Glucametacin, Isozepac, Lonazolac, Metiazinic Acid, Oxametacine, Proglumetacin, Sulindac, Tiaramide and Tolmetin;

Arylbutyric Acid Derivatives such as Butibufen and Fenbufen;

Arylcarboxylic Acids such as Clidanac, Ketorolac and Tinoridine;

Arylpropionic Acid Derivatives such as Bucloxic Acid, Carprofen, Fenoprofen, Flunoxaprofen, Ibuprofen, Ibuproxam, Oxaprozin, Piketoprofen, Pirprofen, Pranoprofen, Protizinic and Tiaprofenic Add;

Pyrazoles such as Mepirizole;

Pyrazolones such as Clofezone, Feprazone, Mofebutazone, Oxyphenbutazone, Phenylbutazone, Phenyl Pyrazolidininones, Suxibuzone and Thiazolinobutazone;

Salicylic Acid Derivatives such as Bromosaligenin, Fendosal, Glycol Salicylate, Mesalamine, 1-Naphthyl Salicylate, Olsalazine and Sulfasalazine;

Thiazinecarboxamides such as Droxicam, Isoxicam and Piroxicam;

Others such as e-Acetamidocaproic Acid, S-Adenosylmethionine, 3-Amino-4-hydroxybutyric Acid, Amixetrine, Bendazac, Bucolome, Carbazones, Difenpiramide, Ditazol, Guaiazulene, Heterocyclic Aminoalkyl Esters of Mycophenolic Acid and Derivatives, Nabumetone, Nimesulide, Orgotein, Oxaceprol, Oxazole Derivatives, Paranyline, Pifoxime, 2-substituted-4,6-di-tertiary-butyl-s-hydroxy-1,3-pyrimidines, Proquazone and Tenidap.

g. Antiseptics

Guanidines such as Alexidine, Ambazone, Chlorhexidine and Picloxydine;

Halogens/Halogen Compounds such as Bornyl Chloride, Calcium Iodate, Iodine, Iodine Monochloride, Iodine Trichloride, Iodoform, Povidone-Iodine, Sodium Hypochlorite, Sodium Iodate, Symclosene, Thymol Iodide, Triclocarban, Triclosan and Troclosene Potassium;

Nitrofurans such as Furazolidone, 2-(Methoxymethyl)-5-Nitrofuran, Nidroxyzone, Nifuroxime, Nifurzide and Nitrofurazone;

Phenols such as Acetomeroctol, Chloroxylenol, Hexachlorophene, 1-Naphthyl Salicylate, 2,4,6-Tribromo-m-cresol and 3',4',5-Trichlorosalicylanilide;

Quinolines such as Aminoquinuride, Chloroxine, Chlorquinaldol, Cloxyquin, Etheylhydrocupreine, Halquinol, Hydrastine, 8-Hydroxyquinoline and Sulfate; and others, such as Boric Acid, Chloroazodin, m-Cresyl Acetate, Cupric sulfate and Ichthammol.

h. Antivirals

Purines/Pyrimidinones, such as 2-Acetyl-Pyridine 5-((2-pyridylamino)thiocarbonyl) Thiocarbonohydrazone, Acyclovir, Dideoxyadenosine, dideoxycytidine, Dideoxyinosine, Edoxudine, Floxuridine, Ganciclovir, Idoxuridine, MADU, Pyridinone, Trifluridine, Vidrarbine and Zidovudline;

Others such as Acetylleucine Monoethanolamine, Acridinamine, Alkylisooxazoles, Amantadine, Amidinomycin, Cuminaldehyde Thiosemicarbzone, Foscarnet Sodium, Kethoxal, Lysozyme, Methisazone, Moroxydine, Podophyllotoxin, Ribavirin, Rimantadine, Stallimycin, Statolon, Thymosins, Tromantadine and Xenazoic Acid.

In certain embodiments, lactam compounds of the present invention, and particulary lactam compounds of formulae (VII) and (IX), have been characterized in opioid receptor binding assays and show preferential binding to κ opioid receptors relative to $\mu$ and δ opioid receptors. In certain embodiments, the invention is directed to methods of binding opioid receptors, including κ opioid receptors, in a patient in need thereof, comprising the step of administering to the patient an effective amount of a compound of formula I. In certain preferred embodiments, the invention is directed to methods of binding κ opioid receptors, wherein said κ opioid receptors are located in the central nervous system. In other preferred embodiments, the invention is directed to methods of binding κ opioid receptors, wherein said κ opioid receptors are located peripherally to the central nervous system. In yet further preferred embodiments, the invention is directed to methods of binding opioid receptors, wherein said binding agonizes the activity of said opioid receptors. In other preferred embodiments, the invention is directed to methods of binding opioid receptors, wherein the compound of formula I does not substantially cross the blood-brain barrier.

In yet another embodiment, the invention is directed to methods for preventing or treating gastrointestinal dysfunction comprising the step of administering to a patient in need thereof, a composition comprising an effective amount of a compound of formula I.

In other embodiments, the invention is directed to methods for preventing or treating ileus comprising the step of administering to a patient in need thereof, a composition comprising an effective amount of a compound of formula I.

In another embodiment, the invention is directed to methods for preventing or treating pain comprising the step of administering to a patient in need thereof, a composition comprising an effective amount of an opioid and an effective amount of a compound of formula I.

In another embodiment, the invention is directed to methods for preventing or treating pruritic dermatoses and conditions characterized by pruritic dermatosis as a symptom, including allergic dermatitis, atopy, contact dermatitis, psoriasis, eczema, opioid-induced pruritus, and insect bites, comprising the step of administering to a patient in need thereof, a composition comprising an effective amount of a compound of formula I.

In another embodiment, the invention is directed to methods for preventing or treating cerebral edema, comprising the step of administering to a patient in need thereof, a composition comprising an effective amount of a compound of formula I.

In other embodiments, the invention is directed to methods for preventing or treating oxygen supply deficiency of the central nervous system, comprising the step of administering to a patient in need thereof, a composition comprising an effective amount of a compound of formula I.

In another embodiment, the invention is directed to methods for inducing Diuresis, comprising the step of administering to a patient in need thereof, a composition comprising an effective amount of a compound of formula I.

In yet another embodiment, the invention is directed to methods for preventing or treating tussis, comprising the step of administering to a patient in need thereof, a composition comprising an effective amount of a compound of formula I.

The lactam derivatives of the present invention may be prepared according to the general method depicted in Scheme 1.

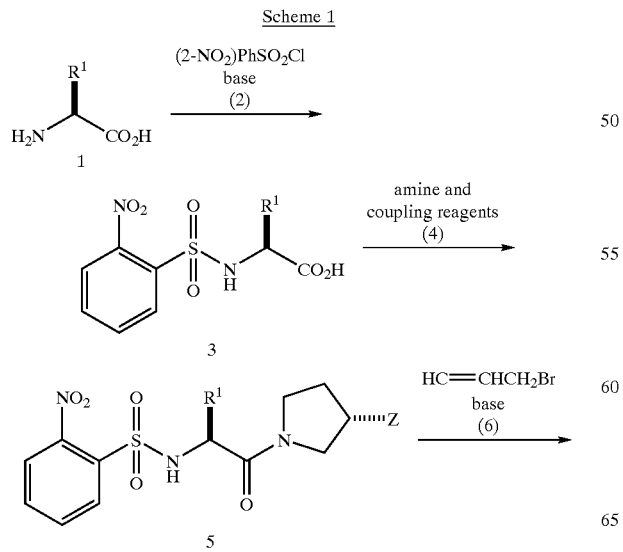

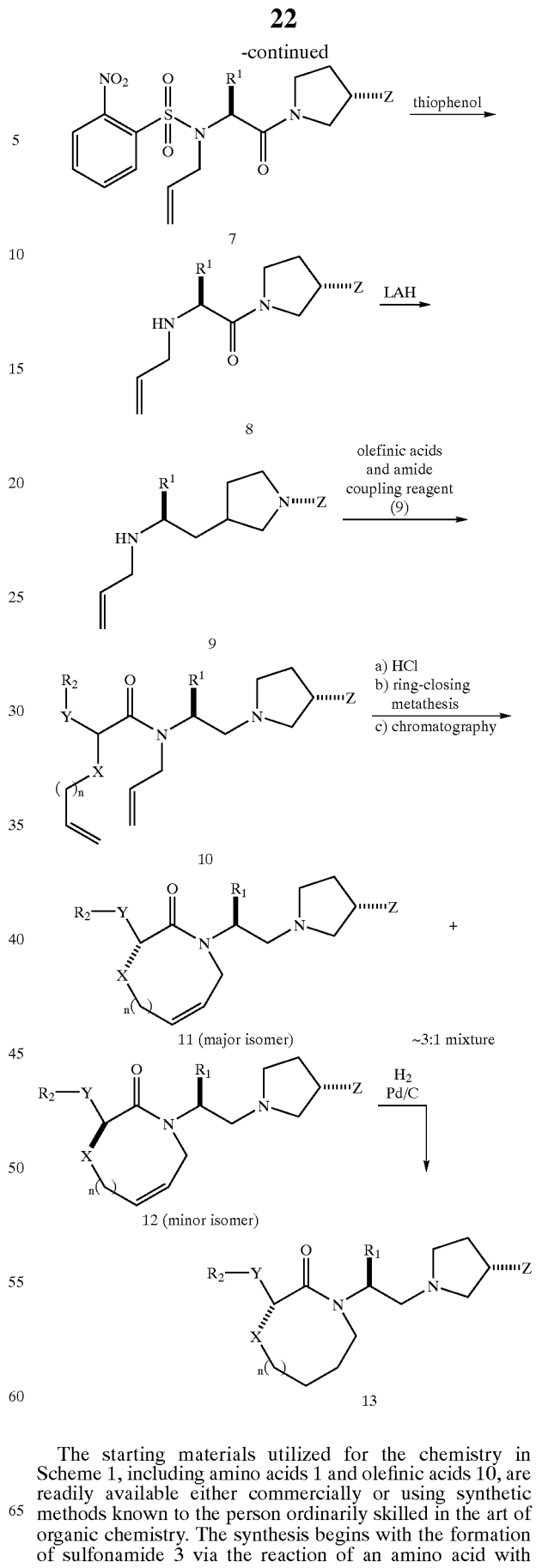

The starting materials utilized for the chemistry in Scheme 1, including amino acids 1 and olefinic acids 10, are readily available either commercially or using synthetic methods known to the person ordinarily skilled in the art of organic chemistry. The synthesis begins with the formation of sulfonamide 3 via the reaction of an amino acid with 2-nitrophenylsulfonyl chloride in the presence of a base. The preferred solvent for the reaction is a water-miscible ether such as tetrahydrofuran or dioxane while the preferred base is aqueous sodium hydroxide. The reaction is conveniently carried out at room temperature. Compound 3 is then coupled to an amine 4 to give amide 5. The preferred coupling reagent is dicyclohexylcarbodiimide in the presence of hydroxybenzotriazole hydrate with the reaction conducted in an ethereal solvent such as tetrahydrofuran. The reaction is initiated at 0° C., and warmed to room temperature after approximately 1 hour, and then allowed to proceed further for 16–24 hours. Next, amide 5 is N-alkylated with allyl bromide using a mild base such as potassium or sodium carbonate in dimethylformamide (DMF) to give 7. The sulfonamide group in 7 is then removed upon treatment with thiophenol for 12–24 hours in a polar non-protic solvent, such as DMF, to give monoamine 8 which in turn is reduced with a reducing agent such as lithium aluminum hydride to give diamine 9. (See Larock, Richard C., *Comprehensive Organic Transformations*, p. 432–434, VCH Publishers, Inc., 1989, for examples of alternative reducing agents for this transformation.). The reduction reaction (8 to 9) can be carried out in an ethereal solvent, such as THF or dioxane, and although the reduction proceeds at a range of temperatures (0 to 60° C.) and times (1–24 hours) it is preferable to conduct the reaction at room temperature for 12–16 hours. The diamine 9 is next coupled to carboxylic acid 10 containing an either a 2-allyl, 2-homoallyl, 2-oxyallyl, or 2-oxyhomoallyl substituent. Coupling is carried out under a variety of conditions, although a preferable coupling reagent is the commercially available 2-chloro-1-methylpyridinium iodide in the presence of a tertiary base such as triethylamine. Because of the rather sterically hindered nature of the diamine 9, the coupling reaction requires approximately two days to go to completion to give diene 11. The diene derivative 11 is subsequently cyclized (ring closing) as the hydrochloride salts in a metathesis reaction using a Grubb's ruthenium catalyst in chlorinated solvent such as dichloromethane under an inert atmosphere, such as nitrogen or argon, at 40–60° C. for 12–24 hours to provide unsaturated lactam derivatives 12 and 13. The ratio is of 12 versus 13 is approximately 2:1 to 3:1 in favor of the stereochemical assignment shown in Scheme 1 where the stereochemistry at $R^1$ is trans relative to the alpha-center in the medium-sized ring. Compounds 12 and 13 are separated by silica column chromatography or reverse phase high-pressure liquid chromatography (HPLC). Compounds with the stereochemistry depicted in 12 (i.e., the major isomer obtained in the reaction) generally have the highest affinity and selectivity for the kappa receptor. Unsaturated lactam derivatives 12 (or 13) are reduced by catalytic hydrogenation with palladium metal deposited on carbon in methanol under an ambient pressure of hydrogen gas to furnish the lactam derivative 14.

The present invention will now be illustrated by reference to the following specific, non-limiting examples. Those skilled in the art of organic synthesis may be aware of still other synthetic routes to the invention compounds. The reagents and intermediates used herein are either commercially available or prepared according to standard literature procedures.

EXAMPLES

The following Examples 1–22 were prepared using the general procedures outlined above.

Example 1

1-(1-(S)-Phenyl-2-pyrrolidin-1-yl-ethyl)-3-[3-(pyrrolidine-1-sulfonyl)-phenyl]-1,3,4,7-tetrahydro-azepin-2-one

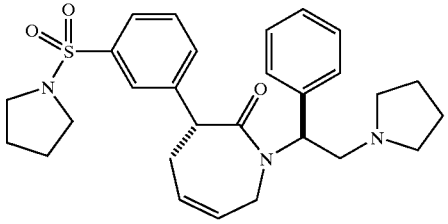

Step A: 2-Nitro-benzenesulfonylamino)-1-(S)-phenyl-acetic acid

To a stirred solution of 1 N sodium hydroxide (725 cm³, 725 mmol) was added (S)—(F)-2 phenylglycine (100.0 g, 662 mmol) that dissolved after 30 minutes at ambient temperature. Tetrahydrofuran (500 cm³) was added at ambient temperature and the solution cooled to 0° C. in an ice bath. Simultaneously both 6N sodium hydroxide (100 cm³, 600 mmol) and 2-Nitrobenzenesulfonyl chloride (154.9 g, 695 mmol) dissolved in tetrahydrofuran (225 cm³) were added dropwise with stirring at 0° C. over 1 hour. The solution was allowed to warm and stir at ambient temperature for 20 hours. Volatile fractions were removed in vacuo and the aqueous solution acidified with 6N hydrochloric acid to pH 1.0 to form a precipitate. The mixture was vacuum filtered to afford a yellow precipitate. The precipitate was washed with water (3×100 ml) and vacuum dried at 50° C. to a constant weight to afford the title compound as a yellow solid (188.2 g, 84.6%) with a negative ion ESI (M–H)– 335.2.

Step B: 2-Nitro-N-(2-oxo-1-(S)-phenyl-2-pyrrolidin-1-yl-ethyl)-benzenesulfonamide To a stirred mixture of 2-nitro-benzenesulfonylamino)-1-(S)-phenyl-acetic acid in two (44.0 g, 131 mmol) batches in anhydrous tetrahydrofuran (1000 cm³) at ambient temperature was added 1-hydroxybenzotriazole hydrate (19.5 g, 144 mmol) followed by pyrrolidine (12.0 cm³, 144 mmol) to afford a solution. The solution was cooled to 0° C. in an ice bath and a 1M solution of 1,3-dicyclohexylcarbodiimide in dichloromethane (144 cm³, 144 mmol) was added over 1 hour to form a thick white precipitate. The mixture was allowed to warm and stir at ambient temperature for 16 hours. The mixture was cooled to 0° C. in an ice bath and the white precipitate vacuum filtered. The volatile fractions were removed in vacuo from the filtrate to afford a crude viscous yellow gum. The crude gum was dissolved in ethyl acetate (1000 cm³), washed with 1 N hydrochloric acid (2×300 cm³), 1 M sodium bicarbonate (1×300 cm³), brine (1×300 cm³), dried over sodium sulfate, vacuum filtered and the volatile fractions removed in vacuo to a viscous yellow gum. The crude product was purified by column chromatography (silica, eluting with hexane-ethyl acetate 3:1 to 0:1) to afford the title compound as a colorless viscous oil (92.6 g, 90.90% o) with a positive ion ESI (M+H)+390.3.

Step C: N-Allyl-2-nitro-N-(2-oxo-1-(S)-phenyl-2-pyrrolidin-1-yl-ethyl)-benzenesulfonamide To a stirred solution of 2-nitro-N-(2-oxo-1-(S)-phenyl-2-pyrrolidin-1-yl-ethyl)-benzenesulfonamide (62.4 g, 160 mmol) in anhydrous dimethylformamide (300 cm³) was added potassium carbonate (44.3 g, 320 mmol). The mixture was stirred at ambient temperature for 10 minutes and allyl bromide (18.0 cm³, 208 mmol) was added dropwise over 10 minutes. The mixture was stirred for 16 hours at ambient temperature and poured into water (2000 cm³) to afford a white precipitate. The mixture was vacuum filtered, washed with water (3×200 cm³) and vacuum dried at 50° C. to constant weight to afford the title compound as a white solid (66.2 g, 96.2%) with a positive ion ESI (M−H)+430.2.

Step D: 2-Allylamino-2-(S)-phenyl-1-pyrrolidin-1-yl-ethanone

To a stirred solution of N-allyl-2-nitro-N-(2-oxo-1-(S)-phenyl-2-pyrrolidin-1-yl-ethyl)-benzenesulfonamide (66.2 g, 154 mmol) in anhydrous dimethylformamide (300 cm³) was added potassium carbonate (63.9 g, 462 mmol). The mixture was stirred at ambient temperature for 10 minutes and thiophenol (22.2 cm³, 216 mmol) was added dropwise over 10 minutes. The mixture was stirred for 16 hours at ambient temperature and poured into water (2000 cm³) and extracted with ethyl acetate (3×500 cm³). The combined ethyl acetate extracts were washed with water (2×400 cm³), brine (1×300 cm³), dried over sodium sulfate, vacuum filtered and the volatile fractions removed in vacuo to a foul smelling yellow oil. The crude product was purified by column chromatography (silica, eluting with hexane-ethyl acetate 1:1 to 0:1 and then dichloromethane-methanol 19:1 to 9:1) to afford the title compound as a yellow viscous oil (31.9 g, 84.9%) with a positive ion ESI (M+H)+245.3.

Step E: Allyl 1-(S)-phenyl-2-pyrrolidin-1-yl-ethyl)-amine

To a stirred solution 2-allylamino-2-(S)-phenyl-1-pyrrolidin-1-yl-ethanone (46.7 g, 191.0 mmol) in anhydrous tetrahydrofuran (700 cm³) cooled to 0° C. in an ice bath was added a 1 M solution of lithium aluminum hydride (191 cm³, 191 mmol) over 20 minutes. The solution was allowed to warm and stir at ambient temperature for 16 hours. The reaction was cooled to 0° C. in an ice bath and quenched with water (7.3 cm³), 15% sodium hydroxide (7.3 cm³) and water (22.0 cm³) to form a white flocculate precipitate. The mixture was vacuum filtered, the precipitate washed with tetrahydrofuran (2×100 cm³) and the filtrate volatile fractions removed in vacuo to afford the title compound as a yellow viscous oil (38.1 g, 86.6%) with a positive ion ESI (M+H)+231.3.

Step F: 2-[3-(Pyrrolidine-1-sulfonyl)-phenyl]-pent-4-enoic acid allyl-(1-(S)-phenyl-2-pyrrolidin-1-yl-ethyl)-amide To a stirred solution of allyl-(1-(S)-phenyl-2-pyrrolidin-1-yl-ethyl)-amine (1.00 g, 4.34 mmol) in dichloromethane (22 cm³) at ambient temperature was added 2-[3-(pyrrolidine-1-sulfonyl)-phenyl]-pent-4-enoic acid (1.34 g, 4.34 mmol) followed by 2-Chloro-1-methylpyridinium iodide (2.22 g, 8.68 mmol) and triethylamine (1.82 cm³, 13.0 mmol) to afford a yellow slurry. The mixture was stirred at ambient temperature for 44 hours to afford a brown solution. The solution was diluted with ethyl acetate (50 cm³) and poured into water (100 cm³). The aqueous was extracted with ethyl acetate (3×30 cm³) and the combined ethyl acetate extracts were washed with 1M sodium bicarbonate (2×50 cm³), brine (1×50 cm³), dried over sodium sulfate, vacuum filtered and the volatile fractions removed in vacuo to a crude brown oil. The crude product was purified by column chromatography (silica, eluting with dichloromethane-methanol 99:1 to 95:5 to afford the title compound as a tan viscous oil (2.10, 92.9%) with a positive ion ESI (M+H)+522.3.

Step G: 1-(1-(S)-Phenyl-2-pyrrolidin-1-yl-ethyl)-3-[3-(pyrrolidine-1-sulfonyl)-phenyl]-1,3,4,7-tetrahydro-azepin-2-one To a stirred solution of 2-[3-(pyrrolidine-1-sulfonyl)-phenyl]-pent-4-enoic acid allyl-(1-(S)-phenyl-2-pyrrolidin-1-yl-ethyl)-amide (2.10 g, 4.03 mmol) in anhydrous dichloromethane (40 cm³) under an atmosphere of dry nitrogen was added 2M HCl in Et₂O (8 cm³, 16 mmol). The solution was stirred at ambient temperature for 30 minutes and the volatile fractions removed in vacuo. The resulting foam was dried at 60° C. under vacuum for 3 hours and dissolved with stirring in anhydrous dichloromethane (100 cm³). Grubb's ruthenium metathesis catalyst (171 mg, 0.202 mmol) was added and dry argon bubbled through the solution for 10 minutes. The solution under dry argon was heated to reflux for 16 hours and cooled to ambient temperature. The solution was treated with tris(hydroxymethyl)phosphine hydrochloride (646 mg, 4.03 mmol) followed by triethylamine (1.12 cm³, 8.06 mmol) and the mixture stirred at ambient temperature for 30 minutes. Water (100 cm³) was added and the mixture was stirred an additional 30 minutes at ambient temperature. The dichloromethane solution was washed with 1 M Na₂CO₃ (2×50 cm³), brine (1×50 cm³), dried over sodium sulfate, vacuum filtered and the volatile fractions removed in vacuo to afford a dark viscous oil (1.99 g, 4.03 mmol) that partially crystallized over time. The crude product was purified by column chromatography (silica, eluting with hexane-ethyl acetate 4:1 to 0:1) to afford two pure title compound diastereoisomers, a minor diastereoisomer (260 mg, 13.1%), positive ion ESI (M+H)+494.3, NMR (400 MHz) δ 7.69–7.74 (3H, m), δ 7.53 (1H, m), δ 7.27–7.33 (5H, m), δ 6.05 (1H, m), δ 5.80 (1H, m), δ 5.72 (1H, m), δ 4.47 (1H, m), δ 3.98 (1H, m), δ 3.27 (6H, m), δ 2.50–2.96 (7H, m), δ 1.76 (8H, m) (typical upper diastereoisomer splitting pattern δ 3.8–6.5) and a major diastereoisomer (576 mg, 29.2%), positive ion ESI (M+H)+494.3, NMR (400 MHz) δ7.65–7.74 (3H, m), δ 7.53 (1H, m) δ 7.26–7.33 (5H, m), δ 6.05 (1H, m), δ 5.66 (1H, m), δ5.42 (1H, m), δ 4.51 (1H, m), δ 4.29 (1H, m), δ 3.26–3.37 (6H, m), δ 2.51–3.06 (7H, m), δ 1.72–179 (8H, m) (typical lower splitting diastereoisomer pattern). The major diastereoisomer was crystallized from methanol (6 cm³) and vacuum filtered to afford tan crystals, m.p. 95–99° C. The absolute stereochemistry was definitively established by X-ray analysis of a single crystal and was performed on a Bruker platform diffractometer equipped with an APEX detector with MoKα radiation, solved by direct methods and completed from subsequent difference Fourier syntheses.

Example 2

1-(1-(S)-Phenyl-2-pyrrolidin-1-yl-ethyl)-3-[3-(pyrrolidine-1-sulfonyl)-phenyl]-azepan-2-one

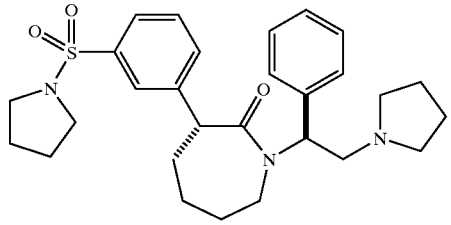

To a stirred solution of 1-(1-(S)-phenyl-2-pyrrolidin-1-yl-ethyl)-3-[3-(pyrrolidine-1-sulfonyl)-phenyl]-1,3,4,7-tetrahydro-azepin-2-one as obtained in Example 1 above (49.4 mg, 1.00 mmol) in anhydrous methanol (5 cm³) was added 5 mg 10% Pd—C. A balloon filled with hydrogen was attached and the flask evacuated 3 times refilling with fresh hydrogen. The solution was stirred at ambient temperature for 16 hours, vacuum filtered through celite, the solid residue washed with methanol (3×5 cm³) and the volatile fractions removed in vacuo to afford the title compound as a white foam (47.8 mg, 96.4%) with a positive ESI (M+H)+ 496.1.

Example 3

N-Methyl-N-{3-[2-oxo-1-(1-(S)-phenyl-2-pyrrolidin-1-yl-ethyl)-2,3,4,7-tetrahydro-1H-azepin-3-yl]-phenyl}-methanesulfonamide: positive ion ESI (M+H)+468.3

Example 4

N-{4-[2-Oxo-1-(1-(S)-phenyl-2-pyrrolidin-1-yl-ethyl)-2,3,4,7-tetrahydro-1H-azepin-3-yl]-benzyl}-methanesulfonamide: positive ion ESI (M+H)+ 468.1

The acid coupled to the diamine was synthesized by the procedure below.

Step 4A: 2-(4-Aminomethyl-phenyl)-pent-4-enoic acid methyl ester

To a stirred solution of commercially available (Astatech) 2-[4-(tert-butoxycarbonylamino-methyl)-phenyl]-pent-4-enoic acid (2.00 g, 6.55 mmol) in methanol (30 cm$^3$) under an atmosphere of dry nitrogen at ambient temperature was added 2M HCl in diethyl ether. The solution was stirred at ambient temperature for 20 hours and the filtrate volatile fractions removed in vacuo to afford the title compound as a white solid (1.67 g, 99.9%) with a positive ion ESI (M+H)+219.2.

Step 4B: 2-[4-(Methanesulfonylamino-methyl)-phenyl]-pent-4-enoic acid methyl ester To a stirred solution of 2-(4-aminomethyl-phenyl)-pent-4-enoic acid methyl ester (1.67 g, 6.55 mmol) in dichloromethane (50 cm$^3$) at ambient temperature under an atmosphere of dry nitrogen was added triethylamine (4.56 cm$^3$, 32.8 mmol) followed by dropwise addition of methanesulfonyl chloride (1.52 cm$^3$, 19.7 mmol) over 5 minutes. The mixture was stirred for 4 hours at ambient temperature and the filtrate volatile fractions removed in vacuo to afford a crude yellow oil. The oil was dissolved in ethyl acetate (100 cm$^3$), washed with saturated sodium bicarbonate (2×50 cm$^3$), brine (25 cm$^3$), dried over sodium sulfate, vacuum filtered and the filtrate volatile fractions removed in vacuo to a crude yellow oil. The oil was purified by column chromatography (silica, eluting with hexane-ethyl acetate 4:1 to 1:1) to afford the title compound as a pale yellow viscous oil (1.85 g, 100%) with a positive ion ESI (M+H)+296.2.

Step 4C: 2-[4-(Methanesulfonylamino-methyl)-phenyl]-pent-4-enoic acid

To a stirred solution of 2-[4-(methanesulfonylamino-methyl)-phenyl]-pent-4-enoic acid methyl ester (1.85 g, 6.55 mmol) in a 1:1 mixture of tetrahydrofuran (25 cm$^3$) and methanol (25 cm$^3$) at ambient temperature under an atmosphere of dry nitrogen was added lithium hydroxide hydrate (1.16 g, 26.2 mmol) dissolved in water (25 cm$^3$). The mixture was stirred at ambient temperature for 16 hours and volatile fractions removed in vacuo to leave an aqueous mixture. The mixture was diluted with water (25 cm$^3$) and acidified with 1 N hydrochloric acid to pH 1.0. The aqueous mixture was extracted with dichloromethane (3×30 cm$^3$), The combined dichloromethane extracts washed with brine (1×30 cm$^3$), dried over sodium sulfate, vacuum filtered and the filtrate volatile fractions removed in vacuo to a colorless oil (1.68 g, 90.7%) with a negative ion ESI (M−H)−282.1.

Example 5

N-Methyl-3-[2-oxo-1-(1-(S)-phenyl-2-pyrrolidin-1-yl-ethyl)-2,3,4,7-tetrahydro-1H-azepin-3-yl]-benzenesulfonamide: positive ion ESI (M+H)+ 454.2

Example 6

N,N-Dimethyl-3-[2-oxo-1-(1-(S)-phenyl-2-pyrrolidin-1-yl-ethyl)-2,3,4,7-tetrahydro-1H-azepin-3-yl]-benzenesulfonamide: positive ion ESI (M+H)+468.3

Example 7

3-[4,5-Dimethoxy-2-(morpholine-4-sulfonyl)-phenyl]-1-(1-(S)-phenyl-2-pyrrolidin-1-yl-ethyl)-1,3,4,7-tetrahydro-azepin-2-one: positive ion ESI (M+H)+570.2

The acid 2-[4,5-dimethoxy-2-(morpholine-4-sulfonyl)-phenyl]-pent-4-enoic acid was synthesized by the procedure below and coupled to the diamine allyl-(1-(S)-phenyl-2-pyrrolidin-1-yl-ethyl)-amine from Example 1 to afford Example 7.

Step 7A: (3,4-Dimethoxy-phenyl)-acetic acid benzyl ester

To a stirred mixture of commercially available 3,4-dimethoxyphenylacetic acid (100.0 g, 510 mmol) in anhydrous 1,2-dichloroethane (500 cm$^3$) at ambient temperature under an atmosphere of dry nitrogen was added thionyl chloride (112 cm$^3$, 1.53 mol) portionwise over 20 minutes. The resulting solution was heated to reflux for 16 hours. The brown solution was cooled to ambient temperature and the volatile fractions removed in vacuo. Residual thionyl chloride was removed by an azeotrope with toluene (3×200 cm$^3$) to afford a crude brown oil. The crude oil was dissolved in anhydrous dichloromethane (400 cm$^3$) and cooled to 0° C. in an ice bath. To the cooled solution was added triethylamine (75 cm$^3$, 535 mmol) dropwise over 10 minutes followed by a solution of benzyl alcohol (50 cm$^3$, 485 mmol) dissolved in anhydrous dichloromethane (200 cm$^3$). The mixture was stirred for 20 hours and warmed to ambient temperature. Water was added to the mixture (700 cm$^3$) and the aqueous extracted with dichloromethane (2×100 cm$^3$). The combined dichloromethane extracts were dried over sodium sulfate, vacuum filtered and the filtrate volatile fractions removed in vacuo to afford a crude brown oil. The crude product was purified by column chromatography (silica, eluting with hexane-ethyl acetate 1:0 to 1:1) to afford the title compound as a pale yellow viscous oil (83.4 g, 57.2%) with a positive ion ESI (M−1H)+287.3.

Step 7B: (2-Chlorosulfonyl-4,5-dimethoxy-phenyl)-acetic acid benzyl

To a stirred solution of (3,4-dimethoxy-phenyl)-acetic acid benzyl ester (83.4 g, 291 mmol) in anhydrous 1,2-dichloroethane (300 cm$^3$) at ambient temperature under an atmosphere of dry nitrogen was added sulfur trioxide N,N-dimethylformamide complex (55.8 g, 364 mol) portionwise over 20 minutes. The mixture was heated to reflux for 20 hours. The tan solution was cooled 0° C. in an ice bath and oxalyl chloride was added cautiously (vigorous gas evolution) over 20 minutes to the cooled solution. The solution was stirred and warmed to ambient temperature over 2 hours. The solution was cooled to 0° C. in an ice bath and water (200 cm$^3$) added cautiously (exothermic). The aqueous was extracted with dichloromethane (2×100 cm$^3$) and the combined dichloromethane extracts were dried over sodium sulfate, vacuum filtered and the filtrate volatile fractions removed in vacuo to afford the title compound as a tan solid (111.1 g, 99.1%), NMR but no ESI (M+H or M−H).

Step 7C: [4,5-Dimethoxy-2-(morpholine-4-sulfonyl)-phenyl]-acetic acid benzyl ester To a stirred mixture of (2-chlorosulfonyl-4,5-dimethoxy-phenyl)-acetic acid benzyl ester (15.0 g, 39.0 mmol) in anhydrous tetrahydrofuran (45 cm$^3$) cooled to 0° C. in an ice bath under an atmosphere of dry nitrogen was added triethylamine (6.00 cm$^3$, 43 mmol). The mixture was stirred 2 minutes and morpholine (3.75 cm$^3$, 43 mmol) was added dropwise to form a solid mass. To efficiently stir the mixture additional anhydrous tetrahydrofuran (145 cm$^3$) was added and the mixture was warmed to ambient temperature over 20 hours. Water was added to the mixture and extracted with ethyl acetate (2×100 cm$^3$). The combined ethyl acetate extracts were dried over sodium sulfate, vacuum filtered and the filtrate volatile fractions removed in vacuo to afford a crude tan solid. The crude solid was recrystallized from toluene (150 cm$^3$) to afford the title compound as tan crystals (10.2 g, 60.2%) with a positive ion ESI (M+H)+436.2.

Step 7D: 2-[4,5-Dimethoxy-2-(morpholine-4-sulfonyl)-phenyl]-pent-4-enoic acid benzyl ester To a stirred mixture of [4,5-dimethoxy-2-(morpholine-4-sulfonyl)-phenyl]-acetic acid benzyl ester (3.00 g, 6.89 mmol) in anhydrous tetrahydrofuran (50 cm$^3$) under an atmosphere of dry nitrogen cooled to −78° C. in an dry ice/acetone bath was added a 1 M solution of lithium bis(trimethylsilyl)amide (7.60 cm$^3$, 7.60 mmol) in tetrahydrofuran dropwise over 5 minutes. The mixture was warmed to 0° C. in an ice bath for 30 minutes to dissolve all solids and cooled again to −78° C. in an dry ice/acetone bath. Neat allyl bromide (0.720 cm$^3$, 8.27 mmol) was added at −78° C. over 5 minutes and the solution warmed to ambient temperature over 2 hours. Saturated ammonium chloride solution (30 cm$^3$) was added and extracted with ethyl acetate (3×40 cm$^3$). The combined ethyl acetate extracts were washed with brine solution (30 cm$^3$), dried over sodium sulfate, vacuum filtered and the filtrate volatile fractions removed in vacuo to afford the title compound as a golden oil (3.25 g, 99.4%) with a positive ion ESI (M+H)+476.3.

Step 7E: 2-[4,5-Dimethoxy-2-(morpholine-4-sulfonyl)-phenyl]-pent-4-enoic acid

To a stirred mixture 2-[4,5-dimethoxy-2-(morpholine-4-sulfonyl)-phenyl]-pent-4-enoic acid benzyl ester (3.25 g, 6.83 mmol) in methanol (28 cm$^3$) under an atmosphere of dry nitrogen was added sodium hydroxide (820 mg, 20.5 mmol) dissolved in water (7 cm$^3$). The mixture completely dissolved while stirring at ambient temperature for 20 hours. The volatile fractions were removed in vacuo and water (30 cm$^3$) was added to the mixture. The aqueous mixture acidified with 6N HCl to pH 1.0 and was extracted with dichloromethane (3×30 cm$^3$). The combined extracts were washed with brine (30 cm$^3$), dried over sodium sulfate, vacuum filtered and the filtrate volatile fractions removed in vacuo to a crude golden oil. The oil was triturated in Et$_2$O (30 cm$^3$), vacuum filtered, washed with Et$_2$O (2×10 cm$^3$) and vacuum dried to constant weight to afford the title compound as (2.30 g, 87.54%) with a positive ion ESI (M+H)+386.2.

Example 8

3-[4,5-Dimethoxy-2-(morpholine-4-sulfonyl)-phenyl]-1-[2-(3-hydroxy-pyrrolidin-1-yl)-1-(S)-phenyl-ethyl]-1,3,4,7-tetrahydro-azepin-2-one: positive ion ESI (M+H)+437.3

The diamine 1-(2-allylamino-2-(S)-phenyl-ethyl)-pyrrolidin-3-(S)-ol similar to the diamine from Example 1 was synthesized by the procedure below and coupled to the acid 2-[4,5-dimethoxy-2-(morpholine-4-sulfonyl)-phenyl]-pent-4-enoic acid from Example 7 to afford Example 8.

Step 8A: N-[2-(3-(S)-Hydroxy-pyrrolidin-1-yl)-2-oxo-1-(S)-phenyl-ethyl]-2-nitro-benzenesulfonamide To a stirred mixture of (2-nitro-benzenesulfonylamino)-1-(S)-phenyl-acetic acid in two (50.0 g, 149 mmol) batches in anhydrous tetrahydrofuran (1000 cm$^3$) at ambient temperature was added 1-hydroxybenzotriazole hydrate (22.1 g, 164 mmol) followed by (S)-2-hydroxypyrrolidine hydrochloride (20.2 g, 164 mmol) commercially available from Astatech. The mixture was cooled to 0° C. in an ice bath and diisopropylethylamine (28.5 cm$^3$, 164 mmol) was added followed by a 1M solution of 1,3-dicyclohexylcarbodiimide in dichloromethane (164 cm$^3$, 164 mmol) over 1 hour to form a thick white precipitate. The mixture was allowed to warm and stir at ambient temperature for 48 hours. The mixture was cooled to 0° C. in an ice bath and the white precipitate vacuum filtered. The volatile fractions were removed in vacuo from the filtrate to afford a crude viscous yellow semisolid. The semisolid was partially dissolved in ethyl acetate (1000 cm$^3$), vacuum filtered, washed with 1 N hydrochloric acid (2×300 cm$^3$), 1 M sodium bicarbonate (1×300 cm$^3$), brine (1×300 cm$^3$), dried over sodium sulfate, vacuum filtered and the volatile fractions removed in vacuo to afford the title compound as a yellow solid (69.8 g, 57.9%) with a positive ion ESI (M+H)+406.2.

Step 8B: N-Allyl-N-[2-(3-(S)-hydroxy-pyrrolidin-1-yl)-2-oxo-1-(S)-phenyl-elthyl]-2-nitro-benzenesulfonamide To a stirred solution of N-[2-(3-(S)-hydroxy-pyrrolidin-1-yl)-2-oxo-1-(S)-phenyl-ethyl]-2-nitro-benzenesulfonamide (62.8 g, 155 mmol) in anhydrous dimethylformamide (300 cm$^3$) was added potassium carbonate (42.8 g, 310 mmol). The mixture was stirred at ambient temperature for 10 minutes and allyl bromide (17.5 cm$^3$, 202 mmol) was added dropwise over 10 minutes. The mixture was stirred for 16 hours at ambient temperature and poured into water (2000 cm$^3$) to afford a yellow gummy precipitate. The gummy precipitate was vacuum filtered, dissolved in ethyl acetate (1000 cm$^3$), washed with water (3×200 cm$^3$), vacuum filtered and the volatile fractions removed in vacuo to afford the title compound as a pale yellow solid (67.1 g, 97.2%) with a positive ion ESI (M+H)+446.2.

Step 8C: N-Allyl-N-{2-[3-(S)-(tert-butyl-dimethyl-silanyloxy)-pyrrolidin-1-yl]-2-oxo-1-(S)-phenyl-ethyl}-2-nitro-benzenesulfonamide To a stirred solution N-allyl-N-[2-(3-(S)-hydroxy-pyrrolidin-1-yl)-2-oxo-1-(S)-phenyl-ethyl]-2-nitro-benzenesulfonamide (7.13 g, 16.0 mmol) in anhydrous dimethylformamide (16 cm$^3$) was added imidazole (2.18 g, 32.0 mmol). When the imidazole dissolved tert-butyldimethylsilyl chloride was added and stirred at ambient temperature for 3 hours. The solution was poured into water (200 cm$^3$), extracted with ethyl ether (3×50 cm$^3$), washed with water (2×40 cm$^3$), brine (40 cm$^3$), dried over sodium sulfate, vacuum filtered and the volatile fractions removed in vacuo to a yellow glass (8.73 g, 97.4%) with a positive ion ESI (M+H)+560.3

Step 8D: 2-Allylamino-1-[3-(S)-(tert-butyl-dimethyl-silanyloxy)-pyrrolidin-1-yl]-2-(S)-phenyl-ethanone To a stirred solution N-allyl-N-{2-[3-(S)-(tert-butyl-dimethyl-silanyloxy)-pyrrolidin-1-yl]-2-oxo-1-(S)-phenyl-ethyl}-2-nitro-benzenesulfonamide (8.73 g, 15.6 mmol) in anhydrous dimethylformamide (45 cm$^3$) was added potassium carbonate (6.50 g, 46.8 mmol). The mixture was stirred at ambient temperature for 10 minutes and thiophenol (2.25 cm$^3$, 21.8 mmol) was added dropwise over 10 minutes. The mixture was stirred for 16 hours at ambient temperature and poured into water (500 cm³) and extracted with ethyl acetate (3×150 cm³). The combined ethyl acetate extracts were washed with water (2×100 cm³), brine (1×100 cm³), dried over sodium sulfate, vacuum filtered and the volatile fractions removed in vacuo to a foul smelling yellow oil. The crude product was purified by column chromatography (silica, eluting with hexane-ethyl acetate 1:1 to 0:1) to afford the title compound as a yellow viscous oil (5.67 g, 97.1%) with a positive ion ESI (M+H)+375.2.

Step 8E: 1-(2-Allylamino-2-(S)-phenyl-ethyl)-pyrrolidin-3-(S)-ol

To a stirred solution of 2-allylamino-1-(3-(S)-hydroxy-pyrrolidin-1-yl)-2-(S)-phenyl-ethanone (5.65 g, 15.1 mmol) in anhydrous tetrahydrofuran (60 cm³) cooled to 0° C. in an ice bath was added a 1 M solution of lithium aluminum hydride (22.6 cm³, 22.7 mmol) over 20 minutes. The solution was allowed to warm and stir at ambient temperature for 16 hours. The reaction was cooled to 0° C. in an ice bath and quenched with water (0.860 cm³), 15% sodium hydroxide (0.860 cm³) and water (2.60 cm³) to form a white flocculate precipitate. The mixture was vacuum filtered, the precipitate washed with tetrahydrofuran (5×30 cm³) and the filtrate volatile fractions removed in vacuo to afford a crude yellow oil. The crude product was purified by column chromatography (silica, eluting with dichloromethane-methanol-ammonium hydroxide 97:3:0 to 90:10:1) to afford the title compound as a yellow viscous oil (2.54 g, 68.3%) with a positive ion ESI (M+H)+247.2.

Example 9

3-(3,4-Dichloro-phenyl)-1-(1-(S)-phenyl-2-pyrrolidin-1-yl-ethyl)-1,3,4,7-tetrahydro-azepin-2-one: positive ion ESI (M+H)+429.3

Example 10

3-(3,4-Dichloro-phenyl)-1-[2-(3-(S)-hydroxy-pyrrolidin-1-yl)-1-(S)-phenyl-ethyl]-1,3,4,7-tetrahydro-azepin-2-one: positive ion ESI (M+H)+445.3

Example 11

3-(3,4-Dichloro-phenoxy)-1-(1-(S)-phenyl-2-pyrrolidin-1-yl-ethyl)-1,3,4,7-tetrahydro-azepin-2-one: positive ion ESI (M+H)+445.0

Step 11A: (3,4-Dichloro-phenoxy)acetic acid allyl ester

To a solution of commercially available (3,4-dichloro-phenoxy)-acetic acid (2.65 g, 12.0 mmol) in allyl alcohol (12.0 cm³, 180 mmol) at ambient temperature under an atmosphere of dry nitrogen was added 4 drops concentrated sulfuric as a catalyst. The solution was stirred at ambient temperature for 20 hours and the volatile fractions removed in vacuo. The residue was dissolved in ethyl ether (50 cm³), washed with water (25 cm³), washed with saturated sodium bicarbonate (25 cm³), washed with brine (25 cm³), dried over magnesium sulfate, vacuum filtered and the filtrate volatile fractions removed in vacuo to afford the title compound as a colorless viscous oil (3.02 g, 96.8%) with positive ion ESI (M+H)+261.3.

Step 11B: 2-(3,4-Dichloro-phenoxy)-pent-4-enoic acid

To a stirred solution of anhydrous tetrahydrofuran (100 cm³) cooled to −100° C. in an ethyl ether/liquid nitrogen bath under an atmosphere of dry nitrogen was added a 2M solution of lithium diisopropylamide (6.30 cm³, 12.7 mmol) in tetrahydrofuran followed by dropwise addition at −100° C. of a solution of (3,4-dichloro-phenoxy)-acetic acid allyl ester (3.00 g, 11.5 mmol) in anhydrous tetrahydrofuran (15 cm³) over 5 minutes. The solution was stirred at −100° C. for 1 hour and the supernatant (3.30 cm³, 11.8 mmol) of a centrifuged 1:1 mixture of chlortrimethylsilane and triethylamine was added dropwise over 5 minutes at −100° C. The solution was stirred an additional 1 hour at −100° C. and allowed to warm to ambient temperature. To the solution was added 1 N sodium hydroxide (250 cm³) and the mixture stirred 10 minutes at ambient temperature. The aqueous layer was separated, extracted with ethyl ether (2×50 cm³) and acidified with 1 N HCl to pH 1.0. The acidified aqueous was extracted with ethyl ether (3×50 cm³), the combined ethyl ether extracts washed with brine (50 cm³), dried over magnesium sulfate, vacuum filtered and the filtrate volatile fractions removed in vacuo to afford a 4:1 mixture of the title compound and (3,4-dichloro-phenoxy)-acetic acid as a pale yellow solid (1.12 g, 37.3%) with negative ESI (M−H)−260.1.

Example 12

3-(4-Chloro-phenyl)-1-(1-(S)-phenyl-2-pyrrolidin-1-yl-ethyl)-1,3,4,7-tetrahydro-azepin-2-one: positive ion ESI (M+H)+395.3

Example 13

3-(3-Chloro-phenyl)-1-(1-(S)-phenyl-2-pyrrolidin-1-yl-ethyl)-1,3,4,7-tetrahydro-azepin-2-one: positive ion ESI (M+H)+395.3

Example 14

3-(2-Chloro-phenyl)-1-(1-(S)-phenyl-2-pyrrolidin-1-yl-ethyl)-1,3,4,7-tetrahydro-azepin-2-one: positive ion ESI (M+H)+395.3

Example 15

3-(4-Methoxy-phenyl)-1-(1-(S)-phenyl-2-pyrrolidin-1-yl-ethyl)-1,3,4,7-tetrahydro-azepin-2-one: positive ion ESI (M+H)+391.3

Example 16

1-(1-(S)-Phenyl-2-pyrrolidin-1-yl-ethyl)-3-(4-trifluoromethyl-phenyl)-1,3,4,7-tetrahydro-azepin-2-one: positive ion ESI (M+H)-t429.3

Example 17

3-Biphenyl-4-yl-1-(1-(S)-phenyl-2-pyrrolidin-1-yl-ethyl) 1,3,4,7-tetrahydro-azepin-2-one: positive ion ESI (M+H)+437.3

Example 18

3-(4-Chloro-phenyl)-1-(1-(S)-phenyl-2-pyrrolidin-1-yl-ethyl)-3,4,5,8-tetrahydro-1H-azocin-2-one: positive ion ESI (M+I)+409.2

Example 19

2-(2-Chloro-phenyl)-4-(1-(S)-phenyl-2-pyrrolidin-1-yl-ethyl)-5,8-dihydro-4H-[1,4]oxazocin-3-one: positive ion ESI (M+H)+411.2

Example 20

2-(4-Methoxy-phenyl)-4-(1-(S)-phenyl-2-pyrrolidin-1-yl-ethyl)-5,8-dihydro-4H-[1,4]oxazocin-3-one: positive ion ESI (M+H)+407.3

Example 21

4-(1-(S)-Phenyl-2-pyrrolidin-1-yl-ethyl)-2-(4-trifluoromethyl-phenyl)-5,8-dihydro-4H-[1,4]oxazocin-3-one: positive ion ESI (M+H)+445.2

Example 22

2-(R)-Phenyl-4-(1-(S)-phenyl-2-pyrrolidin-1-yl-ethyl)-5,8-dihydro-4H-[1,4]oxazocin-3-one: positive ion ESI (M+H)+377.2

Biological Assays

Assessment of Analgesic Activity

The pharmacological activity of the compounds of the present invention may be assessed by several art-recognized in vitro and in vivo models. Some of the typical models are described herein.

(a) In Vitro Binding Assay (Primary Screen)

The potencies of the compounds of the invention were determined by testing the ability of a range of concentrations of each compound to inhibit the binding of the non-selective opioid antagonist, [$^3$H]diprenorphine, to the cloned human $\mu$, $\kappa$, and $\delta$ opioid receptors, expressed in separate cell lines. $IC_{50}$ values were obtained by nonlinear analysis of the data using GraphPad Prism version 3.00 for Windows (GraphPad Software, San Diego). Ki values were obtained by Cheng-Prusoff corrections of $IC_{50}$ values.

The receptor binding method was a modification of the method of K. Raynor et al. (Mol. Pharmnacol. 1994, 45, 330–334). After dilution in buffer A and homogenization as before, membrane proteins (10–80 $\mu$g) in 250 $\mu$L were added to mixtures containing test compound and [$^3$H]diprenorphine (0.5 to 1.0 nM, 40,000 to 50,000 dpm) in 250 $\mu$L of buffer A in 96-well deep-well polystyrene titer plates (Beckman). After incubation at room temperature for one hour, the samples were filtered through GF/B filters that had been presoaked in a solution of 0.5% (w/v) polyethylenimine and 0.1% (w/v) bovine serum albumin in water. The filters were rinsed 4 times with 1 mL of cold 50 mM Tris HCl, pH 7.8 and radioactivity remaining on the filters determined by scintillation spectroscopy. Nonspecific binding was determined by the minimum values of the titration curves and was confirmed by separate assay wells containing 10 $\mu$M naloxone. $K_i$ values were determined by Cheng-Prusoff corrections of $IC_{50}$ values derived from nonlinear regression fits of 12 point titration curves using GraphPad Prism® version 3.00 for Windows (GraphPad Software, San Diego, Calif.).

To determine the equilibrium dissociation constant for the inhibitors ($K_i$), radioligand bound (cpm) in the presence of various concentrations of test compounds was measured. The concentration to give half-maximal inhibition ($EC_{50}$) of radioligand binding was determined from a best nonlinear regression fit to the following equation, $$Y = \text{Bottom} + \frac{(\text{Top} - \text{Bottom})}{1 + 10^{X - \text{Log}EC50}}$$

where Y is the amount of radioligand bound at each concentration of test compound, Bottom is the calculated amount of radioligand bound in the presence of an infinite concentration of test compound, Top is the calculated amount of radioligand bound in the absence of test compound, X is the logarithm of the concentration of test compound, and LogEC50 is the log of the concentration of test compound where the amount of radioligand bound is half-way between Top and Bottom. The nonlinear regression fit was performed using the program Prism® (GraphPad Software, San Diego, Calif.). The $K_i$ values were then determined from the $EC_{50}$ values by the following equation, $$K_i = \frac{EC_{50}}{1 + \frac{[\text{ligand}]}{K_d}}$$

where [ligand] is the concentration of radioligand and $K_d$ is the equilibrium dissociation constant for the radioligand.

The potencies of the agonists were assessed by their abilities to stimulate [$^{35}$S]GTP$\gamma$S binding to membranes containing the cloned human a receptors.

To determine the $EC_{50}$ value, which was the concentration to give half-maximal stimulation of [$^{35}$S]GTP$\gamma$S binding, the amount of [$^{35}$S]GTP$\gamma$S bound in the presence of various concentrations of agonists was measured. The $EC_{50}$ value was then determined.

(b) Inflamed Knee Joint Hyperalgesia Model and Blood Pressure Response to Compression of the Inflamed Knee Joint Inflammation in a joint is often associated with hyperalgesia (pain during normal flexion and extension and during the application of gentle innocuous pressure) and/or persistent pain (resting pain; Schaible et al., Pain 55: 5–54, 1993). During the course of knee joint inflammation, a cascade of events occurs, which includes: (i) synthesis and release of inflammatory mediators in the joint, (ii) release of neuropeptides from afferent fibers in the joint cavity, and (iii) increased primary afferent outflow from group II, III, IV sensory fibers (Schaible et al., Pain 55: 5–54, 1993). An important result of this cascade is that there is an augmentation in the response of small, lightly myelinated and unmyelinated afferents to low intensity stimuli. In this manner, the peripheral nerve innervating inflamed tissue can evoke an exaggerated behavioral response to otherwise innocuous stimuli, i.e., a state of hyperalgesia. Thus, inflammation of the knee joint will result in increased spontaneous afferent activity, the appearance of an exaggerated discharge with joint flexion and extension (Schaible et al. J. Neurophysiol. 54: 1109–1122, 1993) and signs of a pain-associated autonomic reaction (Sata et al., Neurosci. Lett. 52: 55–60, 1984).

Injection of a mixture of kaolin and carrageenan into the knee joint induces an experimental arthritis. As exemplified below, this treatment was characterized by a reliable increase in joint volume and circumference. In the unanesthetized rat, these joint changes were accompanied by a tendency to avoid weight bearing, suggesting an ongoing pain state. According to electrophysiological studies, in the course of the development of this acute arthritis, C and Ad units normally responding only to extreme joint distortion become activated by slight movement (Schaible et al., J. Neurophysiol. 54: 1109–1122, 1985). Spinal neurons with knee joint receptive fields in the deep dorsal horn of the spinal cord show clear development of hyperexcitability with the acute inflammation in the joint (Neugebauer et al., J. Neurosci. 70: 1365–1377, 1993). This sensitization of group III and IV fibers was observed within 2–3 hours after injection of kaolin and carrageenan into the knee joint, a time course that closely matches the time course of the development of hyperalgesia in the rat knee joint compression model. These observations indicate that spinal cord neurons and joint primary afferent fibers become sensitized and may underlie hyperalgesia observed in this arthritic state. Such afferent input may drive autonomic responses that are typically associated with the processing of input from afferents typically activated by stimuli generated by the local inflammatory state. In addition to the above-mentioned inflamed knee joint mechanism, the blood pressure (BP) changes might also be evoked reflexively by afferent neural activity from receptors located in the skeletal muscle (Williamson et al., *J. Physiol.* 475: 351–357, 1994). This response is dependent on the changes in intramuscular pressure and the quality of muscle mass compressed. This particular mechanical reflex, however, appears to operate independently of the pain response and appears to play a minor role in the exemplified experiments, as inflation of the cuff on the left normal knee joint had no effect upon BP. In any case, it is possible that overflow of the carrageenan from the joint capsule may serve to render surrounding tissue inflamed as well. Sensitization of C and A units was observed in the rat gastroenemius muscle by infiltration with carrageenan (Handwerker et al., *Pain and Inflammation*, Proceeding of the VI$^{th}$ World Congress on Pain, Bond et al. eds., Elsevier Science Publishers BV, pp. 59–70, 1991). Based on these considerations, it appears that compression of the inflamed knee joint yields a noxious stimulus and this in turn activates a sympathetic response resulting in an increase in BP.

Local inflammation of the knee results in a state where otherwise innocuous stimuli results in a prominent autonomic response, including increased blood pressure (BP) and heart rate (see, e.g., Sata et al., *Neurosci. Lett.* 52: 55–60, 1984). Alternatively, neural outflow from the inflamed knee is recorded (see, e.g. Neugebauer et al., *J. Neurosci.* 70: 1365–1377, 1993).

An in vitro test that measures spontaneous discharge in injured skin by topical application may also be used. (see, e.g., Andreev et al., *Neurosci.* 58: 793–798, 1994).

(c) In Vivo Evaluation of Formalin-Induced Nociception

Administration of formalin into the paw results in a localized inflammation and a pain response that is moderate in intensity and continuous in duration. Unlike many other assays of nociception, the formalin assay measures tonic pain that is a result of tissue injury, and therefore is a model which is more relevant to clinical pain states in humans (see Tjolsen et al., *Pain* 51: 5–17, 1992). In the rat the response to formalin-induced pain consists of spontaneous flinching behavior, characterized by paw lifting and paw shaking, and a rapid vibration of the paw after drawing it under the body. The flinching response can be reliably quantitated and exhibits two peaks of activity which are indicative of acute and tonic pain (Wheeler-Aceto and Cowan, *Psychopharmacology* 104: 3544, 1991). The early or acute phase lasts from 0–5 minutes post-formalin and is followed by a quiescent period lasting approximately 15 minutes. The tonic phase occurs from 20–35 minutes following formalin injection and is the interval where the number of flinching responses is maximal. This model has been characterized in several species (Tjolsen et al., *Pain* 51: 5–17, 1992) and is sensitive to the analgesic effects of opiates administered by a variety of routes, including local administration directly into the paw. In addition, the test is particularly sensitive to the effects of kappa. agonists (Wheeler-Aceto and Cowan, *Psychopharmacology* 104: 35–44, 1991).

Inflammation is induced by subcutaneous injection of 50 ml of a 5% formalin solution into the dorsal surface of the right hind paw of male Sprague-Dawley rats weighing 70–90 g. Injections of drug are given into the dorsal surface of the paw prior to formalin injection, and flinching behavior is quantitated by counting the number of responses that occur during the tonic phase of pain, lasting from 20–35 min after formalin injection. Results are expressed as the mean percent antagonism of formalin-induced flinching calculated for individual drug-treated, formalin-injected rats using the following formula:

(mean formalin response−mean saline response)−individual response×100(mean formalin response−mean saline response)

The mean formalin response is the mean behavioral score of vehicle-treated and formalin-injected rats. The mean saline response is the pooled behavioral score from rats injected with 50 ml of saline into the paw.

(d) Randall-Selitto Test

Numerous variations and exemplifications of this assay are known to those of skill in this art (see, Randall et al., *Arch. Int. Pharmacodyn.* 111: 409419, 1957; see, also, e.g., U.S. Pat. No. 5,434,292, U.S. Pat. No. 5,369,131, U.S. Pat. No. 5,345,943, U.S. Pat. No. 5,242,944 and U.S. Pat. No. 5,109,135.

The pain threshold is measured in this method as the amount of pressure in grams required to induce a flight reaction (struggle) when applied to the foot of an experimental animal exhibiting hyperalgesia, typically an inflamed paw, compared to a control, such as the same or equivalent animal in the absence of the inflammation, and/or in the absence of a test compound. Incremental pressure is applied to the paw with a wedge-shaped blunt piston onto the dorsal surface of the hind paw by means of a paw pressure analgesia meter. The pressure required to elicit paw withdrawal, the paw pressure threshold (PPT), is determined.

Stein and coworkers (Stein et al., *Pharmacol. Biochem. Behav.* 31:445–451, 1988; Stein et al., *J. Pharmacol. Exp. Ther.* 248: 1269–1275, 1989) have developed a model of peripheral inflammation and hyperalgesia in rats, which supports the role of opiates in mediating peripheral analgesia. In this protocol, modified Freund's adjuvant is used as the inflammatory stimulus, and the paw pressure test is used to assess the response of the rat to a painful pressure stimulus. The model is sensitive to opiate agonists of the $\mu$, $\delta$ and $\kappa$ subtypes, which produce analgesia upon administration (Antonijevic et al., *J. Neurosci.* 15: 165–172, 1995; Stein et al., *Neurosci. Lett.* 84: 225–228, 1988; Stein et al., *J. Pharmacol. Exp. Ther.* 248: 1269–1275, 1989). Histological verification of opiate receptor localization and density have confirmed that peripheral opiate receptors are accessible on primary afferent nerve fibers and are upregulated following inflammation (Hassan et al., *Neuroscience* 55: 185–193, 1993; Przewlocki et al., *Neuroscience* 48: 491–500, 1992).

Experiments are conducted in rats weighing 150–250 g at the time of inoculation. Modified Freund's complete adjuvant (FCA) is used as the inflammatory stimulus. Rats are administered an i.pl. injection of the FCA suspension into the right hind foot. Hyperalgesia and antinociception are evaluated using the paw pressure test. Fhe rat is gently restrained and incremental pressure is applied to the paw with a wedge-shaped blunt piston onto the dorsal surface of the hind paw by means of a paw pressure analgesia meter. The pressure required to elicit paw withdrawal, the paw pressure threshold (PPT), is determined. A cutoff pressure of 250 g is used to avoid undue stress and pain to the animal. Baseline responding is established by determining the average of three consecutive trials separated by 10 seconds. The same procedure is conducted on the contralateral side and the sequence of sides is alternated between animals to control for order effects. Typically injections are not made in the contralateral (noninflamed) paw; however, in selected cases drugs may be administered to the contralateral paw to evaluate the potential for drug effects in the absence of inflammation.

Analgesic activity is determined by expressing the increase in PPT resulting from the effect of the drug as a percentage of basal pre-injection thresholds.

Hyperalgesia can also be produced by inflammatory stimuli such as yeast or carrageenan, endogenous inflammatory mediators such as bradykinin or prostaglandins, or other types of chemical irritants (see Hargreaves and Joris, *APS Journal* 2: 51–59, 1993).

(e) Acetic Acid-Induced Writhing

This test identifies novel agents that exhibit peripheral analgesic activity against visceral or chemical pain (see Barber and Gottschlich, *Med. Res. Rev.* 12: 525–562, 1986; Ramabadran and Bansinath, *Pharm. Res.* 3: 263–270, 1986). Injection of acetic acid into the peritoneal cavity is used as the noxious stimulus, and the number of writhing responses that occur in response to acetic acid are counted in order to quantif the response to pain. Compounds which possess analgesic activity reduce the number of writhing responses that occur. Opiate agonists of the μ and κ subtype exhibit analgesic activity in this model (Barber and Gottschlich, *Med. Res. Rev.* 12: 525–562, 1986; Millan, *Trends Pharmacol. Sci.* 11: 70–76, 1990). Novel compounds that demonstrate potency and efficacy in this assay are potential drugs for the treatment of various pathological conditions involving peripheral pain.

The writhing assay is adapted from the procedure originally described by Taber et al. (*J. Pharmacol. Exp. Ther.* 169: 29–38, 1986), using male CF-1 mice weighing 20–25 g. Animals are treated with various doses of drugs prior to the administration of an i.p. injection of 0.6% acetic acid solution. Mice are then placed into observation chambers and the number of writhing responses, as defined by a full hind limb extension and retraction, are recorded.

The mean number of writhing responses is calculated for vehicle-treated control mice, and the percent inhibition (% I) of writhing is calculated for each mouse that is treated with drug using the following formula:

% *I*=100×(mean control writhing responses−individual test responses)(mean control writhing responses)

(f) Hyperalgesia Induced by Tape Stripping

The objective of this assay is to identify novel agents which exhibit peripherally-mediated analgesia in circumstances, such as burns and abrasions, which lead to hyperalgesia. In such injuries, the loss of the stratum corneum is followed by an inflammatory response (erythema) and a painful response to otherwise innocuous stimuli. Removal of the stratum corneum by repeated application and removal of cellophane tape, termed tape stripping, has been shown to be a simplified model of these injuries, which share characteristics of first degree burns (see Flynn, *Percutaneous Absorption*, R. L. Bronaugh and H. I. Maibach, eds., Marcel Dekker Inc., pp. 18–42, 1985). This method of barrier disruption avoids the application of potentially toxic chemicals and permits evaluation of peripheral analgesics following topical administration because tape stripping removes the barrier to effective topical therapy (the stratum corneum) while simultaneously resulting in inflammation and hyperalgesia. Tape stripping has been validated in humans as a model for the testing of topical agents (Pershing et al., *Antimicrob. Agents Chemother.* 38: 90–95, 1994; Roy and Flynn, *Pharm. Res.* 7: 842–847, 1990).

Experiments are conducted in male Sprague-Dawley rats weighing 250–500 g at the time of treatment. After anesthesia of the rat with ketamine-xylamine, a 1–3 cm² patch of rat skin is treated by repeated application and removal of tape. This procedure results in removal of the stratum corneum as determined by a glistening appearance of the skin. The tape stripped skin is evaluated for a visible erythema and for sensitivity to contact by heat or pressure stimuli using a focused beam of light by testing in the paw pressure apparatus or by touch with von Frey hairs. The diameter of the von Frey hairs will be selected based on a diameter which causes no response in control rats but has a readily detectable response in treated rats.

Typically analgesics will be formulated in a suitable topical medium and applied to the treated skin. Some rats will receive only the topical medium without analgesic to control for an effect of the topical medium alone. The presence of analgesia is determined by the latency to respond to the heat stimulus or by response to touch or pressure.

Compounds in Examples 1–22 showed kappa receptor affinity (Ki)<10 micromolar. For example, compound of Example 9 had a Ki=1 nM against the human kappa receptor with >100× selectivity versus the human μ and δ receptors and was an agonist with an $EC_{50}$=2.5 nM. Compound of Example 9 exhibited a % A>80% at a dose of 100 μg, i.paw in the in vivo formalin-induced nociception assay. This compound also blocked the action of acetic acid-induced writhing when administered orally with an ED50<30 mg/kg.

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A compound of Formula I:

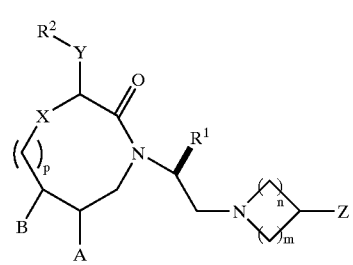

wherein:

A and B are each H, or when taken together with the carbon atoms to which they are attached, form a carbon—carbon double bond;

X is —O— or a single bond;

Y is —O—, —CH$_2$—, or a single bond, provided that when X is —O—, Y cannot be —O—;

Z is H or —OH;

$R^1$ is optionally substituted alkyl, optionally substituted aralkyl, or optionally substituted aryl;

$R^2$ is optionally substituted alkyl, optionally substituted aryl, or —NR$^3$R$^4$ provided that when Y is —O—, $R^2$ cannot be —NR$^3$R$^4$;

m and n are each independently an integer from 1 to 4, and the sum of (m+n) is an integer from 2 to 5;

p is the integer 1 or 2;

$R^3$ is H or optionally substituted alkyl;

R⁴ is —C(=O)R⁵, —C(=O)NR⁵R⁶, —SO₂R⁵, —C(=O)NHR⁶, optionally substituted aryl, or an optionally substituted mono- or multi-cyclic aromatic ring system having from 1 to 50 ring carbon atoms and 1 to 4 ring heteroatoms selected from the group consisting of O, N, and S;

R⁵ is optionally substituted alkyl, optionally substituted cycloalkyl, an optionally substituted mono- or multi-cyclic aliphatic ring system having from 3 to 20 ring carbon atoms and 1 to 4 rine heteroatoms selected from the group consisting of O, N, and S, optionally substituted aralkyl, optionally substituted aryl, or an optionally substituted mono- or multi-cyclic aromatic ring system having from 1 to 50 ring carbon atoms and 1 to 4 ring heteroatoms selected from the group consisting of O, N, and S; and R⁶ is H, optionally substituted alkyl, optionally substituted aryl, optionally substituted aralkyl, or together with the nitrogen atom to which they are attached, R⁵ and R⁶ form a 4–8 membered optionally substituted heterocycloalkyl ring, said heterocycloalkyl ring optionally interrupted by one or more additional heteroatoms selected from nitrogen, oxygen, and sulfur;

or a stereoisomer, pharmaceutically acceptable salt, hydrate, solvate, acid salt hydrate or N-oxide thereof;

wherein said optional substituents are selected from the group consisting of halo, alkyl, cycloalkyl, alkylcycloalkyl, alkenyl, alkynyl, aralkyl, aryl, heteroaryl, heteroaralkyl, spiroalkyl, heterocycloalkyl, hydroxyl (—OH), alkoxyl, aryloxyl, aralkoxyl, nitro (—NO₂), cyano (—CN), amino (—NH₂), -N-substituted amino (—NHR"), -N,N-disubstituted amino (—N(R")R"), carboxyl (—COOH), —C(=O)R", —OR", —C(=O)OR", —NHC(=O)R", aminocarbonyl (—C(=O)NH₂), -N-substituted aminocarbonyl (—C(=O)NHR"), -N,N-disubstituted aminocarbonyl (—C(=O)N(R")R"), thiol, thiolato (SR"), sulfonic acid (SO₃H), phosphonic acid (PO₃H), S(=O)₂R", S(=O)₂NH₂, S(=O)₂NHR", S(=O)₂NR"R", NHS(=O)₂R", NR"S(=O)₂R", CF₃, CF₂CF₃, NHC(=O)NHR", NHC(=O)NR"R", NR"C(=O)NHR", NR"C(=O)NR"R", and NR"C(=O)R", wherein each R" is independently H, alkyl, cycloalkyl, alkenyl, aryl, aralkyl, heteroaryl, or heterocycloalkyl.

2. A compound according to claim 1, of Formula II:

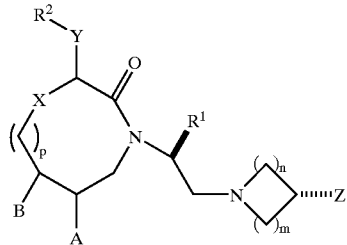

II wherein:
R¹ is optionally substituted alkyl or optionally substituted aryl;
Y is —O— or a single bond; and
R² is optionally substituted alkyl or optionally substituted aryl.

3. A compound according to claim 2, wherein R¹ is optionally substituted aryl.

4. A compound according to claim 2, wherein the sum of (m+n) is the integer 3.

5. A compound according to claim 2, wherein A and B, taken together with the carbon atoms to which they are attached, form a carbon—carbon double bond.

6. A compound according to claim 2, wherein Y is a single bond.

7. A compound of claim 2, wherein R² is optionally substituted aryl.

8. A compound according to claim 7, wherein R² is aryl which is substituted with at least one of halo, alkoxy, mono- or perhaloalkyl, aryl, aryloxy, N(H)SO₂-alkyl, N(alkyl)SO₂-alkyl, CH₂N(H)SO₂-alkyl, CH₂N(alkyl)SO₂-alkyl, and SO₂N(R")R", wherein one of R" is H or alkyl and the other of R" is alkyl or heterocycloalkyl, or together with the nitrogen atom to which they are attached, R" and R" form a 4- to 7-membered heterocycloalkyl ring.

9. A compound according to claim 2, of Formula III:

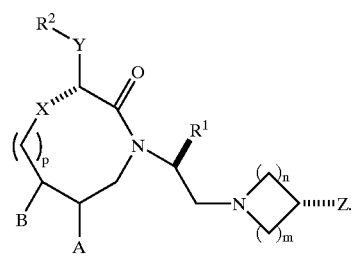

III

10. A compound according to claim 9, of Formula IV:

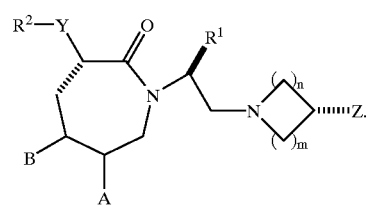

IV

11. A compound according to claim 10, of Formula V:

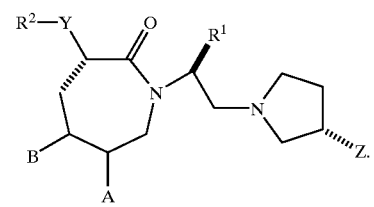

V

12. A compound according to claim 9, of Formula VI:

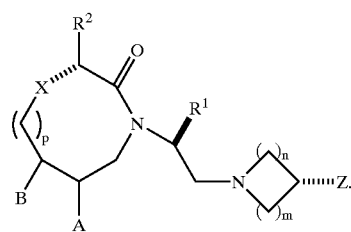

VI

13. A compound according to claim 12, of Formula VII:

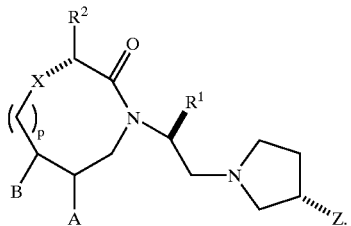

VII

14. A compound according to claim 11, of Formula VIII:

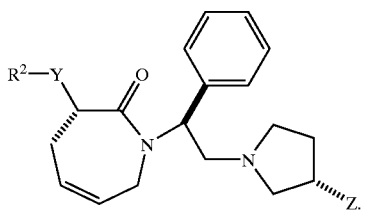

VIII

15. A compound according to claim 14, wherein $R^2$ is optionally substituted aryl.

16. A compound according to claim 15, wherein Y is a single bond.

17. A compound according to claim 16, wherein $R^2$ is aryl which is substituted with at least one of halo, alkoxy, mono- or perhaloalkyl, aryloxy, —NHSO$_2$-alkyl, CH$_2$NHSO$_2$-alkyl, or SO$_2$NR"R", wherein one of R" is H or alkyl and the other of R" is alkyl or heterocycloalkyl.

18. A compound according to claim 13, of Formula IX:

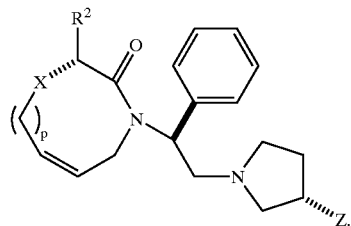

IX

19. A compound according to claim 18, wherein X is a single bond, p is the integer 2, and $R^2$ is optionally substituted aryl.

20. A compound according to claim 18, wherein X is —O—, and $R^2$ is optionally substituted aryl.

21. A pharmaceutical composition, comprising:
a pharmaceutically acceptable carrier; and an effective amount of a compound according to claim 1.

22. A pharmaceutical composition, comprising:
a pharmaceutically acceptable carrier; and an effective amount of a compound according to claim 2.

23. A pharmaceutical composition, comprising:
a pharmaceutically acceptable carrier; and an effective amount of a compound according to claim 9.

24. A pharmaceutical composition, comprising:
a pharmaceutically acceptable carrier; and an effective amount of a compound according to claim 10.

25. A pharmaceutical composition, comprising:
a pharmaceutically acceptable carrier; and an effective amount of a compound according to claim 11.

26. A pharmaceutical composition, comprising:
a pharmaceutically acceptable carrier; and an effective amount of a compound according to claim 12.

27. A pharmaceutical composition, comprising:
a pharmaceutically acceptable carrier; and an effective amount of a compound according to claim 13.

28. A pharmaceutical composition, comprising:
a pharmaceutically acceptable carrier; and an effective amount of a compound according to claim 14.

29. A pharmaceutical composition, comprising:
a pharmaceutically acceptable carrier; and an effective amount of a compound according to claim 17.

30. A pharmaceutical composition, comprising:
a pharmaceutically acceptable carrier; and an effective amount of a compound according to claim 18.

31. A method of binding opioid receptors to treat a condition or disease selected from the group consisting of: gastrointestinal dysfunction, ileus, analgesia, pruritic dermatoses, and conditions characterized by pruritic dermatosis as a symptom, cerebral edema, oxygen supply deficiency of the central nervous system, or tussis in a patient in need thereof, comprising the step of:
administering to said patient an effective amount of a compound according to claim 1.

32. A method according to claim 31, wherein said compound binds κ opioid receptors.

33. A method according to claim 32, wherein said κ opioid receptors are located in the central nervous system.

34. A method according to claim 32, wherein said κ opioid receptors are located peripherally to the central nervous system.

35. A method according to claim 31, wherein said binding agonizes the activity of said opioid receptors.

36. A method according to claim 31, wherein said compound does not substantially cross the blood-brain barrier.

37. A method according to claim 31, wherein said patient is in need of an analgesic.

38. A method for treating gastrointestinal dysfunction, comprising the step of:
administering to a patient in need of such treatment, a composition comprising an effective amount of a compound according to claim 1.

39. A method for treating ileus, comprising the step of:
administering to a patient in need of such treatment, a composition comprising an effective amount of a compound according to claim 1.

40. A method for treating pruritic dermatoses and conditions characterized by pruritic dermatosis as a symptom, comprising the step of:
administering to a patient in need of such treatment, a composition comprising an effective amount of a compound according to claim 1.

41. A method according to claim 40, wherein said pruritic dermatosis is selected from: allergic dermatitis, atopy, contact dermatitis, psoriasis, eczema, opioid-induced pruritus, and insect bites.

42. A method for treating cerebral edema, comprising the step of:
administering to a patient in need of such treatment, a composition comprising an effective amount of a compound according to claim 1.

43. A method for treating oxygen supply deficiency of the central nervous system, comprising the step of:
administering to a patient in need of such treatment, a composition comprising an effective amount of a compound according to claim 1.

44. A method for inducing diuresis, comprising the step of:
administering to a patient in need thereof, a composition comprising an effective amount of a compound according to claim 1.

45. A method for treating tussis, comprising the step of:
administering to a patient in need thereof, a composition comprising an effective amount of a compound according to claim 1.

46. A compound of claim 1, wherein:
$R^4$ is —C(=O)$R^5$, —C(=O)N$R^5R^6$, —SO$_2R^5$, —C(=O)NH$R^6$, optionally substituted aryl, or an optionally substituted mono- or multi-cyclic aromatic ring system having from 3 to 50 ring carbon atoms and 1 to 4 ring heteroatoms selected from the group consisting of O, N, and S.

47. A compound of claim 46, wherein:
$R^4$ is —C(=O)$R^5$, —C(=O)N$R^5R^6$, —SO$_2R^5$, —C(=O)NH$R^6$, optionally substituted aryl, or an optionally substituted mono- or multi-cyclic aromatic ring system having from 4 to 10 ring carbon atoms and 1 to 4 ring heteroatoms selected from the group consisting of O, N, and S; and
$R^5$ is optionally substituted alkyl, optionally substituted cycloalkyl, an optionally substituted mono- or multi-cyclic aliphatic ring system having from 4 to 10 ring carbon atoms and 1 to 4 ring heteroatoms selected from the group consisting of O, N, and S, optionally substituted aralkyl, optionally substituted aryl, or an optionally substituted mono- or multi-cyclic aromatic ring system having from 4 to 10 ring carbon atoms and 1 to 4 ring heteroatoms selected from the group consisting of O, N, and S.

48. A compound of Formula I:

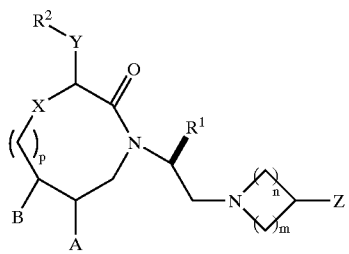

I wherein:
A and B are each H, or when taken together with the carbon atoms to which they are attached, form a carbon—carbon double bond;
X is —O— or a single bond;
Y is —O—, —CH$_2$—, or a single bond, provided that when X is —O—, Y cannot be —O—;
Z is H or —OH;
$R^1$ is optionally substituted alkyl, optionally substituted aralkyl, or optionally substituted aryl;
$R^2$ is optionally substituted alkyl, optionally substituted aryl, or —N$R^3R^4$ provided that when Y is —O—, $R^2$ cannot be —N$R^3R^4$;

m and n are each independently an integer from 1 to 4, and the sum of (m+n) is an integer from 2 to 5;
p is the integer 1 or 2;
$R^3$ is H or optionally substituted alkyl;
$R^4$ is —C(=O)$R^5$, —C(=O)N$R^5R^6$, —SO$_2R^5$, —C(=O)NH$R^6$, optionally substituted aryl, or optionally substituted mono- or multi-cyclic aromatic ring system selected from the group consisting of pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl;
$R^5$ is optionally substituted alkyl, optionally substituted cycloalkyl, an optionally substituted mono- or multi-cyclic aliphatic ring system having from 3 to 20 ring carbon atoms and 1 to 4 ring heteroatoms selected from the group consisting of O, N, and S, optionally substituted aralkyl, optionally substituted aryl, or an optionally substituted mono- or multi-cyclic aromatic ring system selected from the group consisting of pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl; and
$R^6$ is H, optionally substituted alkyl, optionally substituted aryl, optionally substituted aralkyl, or together with the nitrogen atom to which they are attached, $R^5$ and $R^6$ form a 4–8 membered optionally substituted heterocycloalkyl ring, said heterocycloalkyl ring optionally interrupted by one or more additional heteroatoms selected from nitrogen, oxygen, and sulfur;
wherein said optional substituents are selected from the group consisting of halo, alkyl, cycloalkyl, alkylcycloalkyl, alkenyl, alkynyl, aralkyl, aryl, heteroaryl, heteroaralkyl, spiroalkyl, heterocycloalkyl, hydroxyl (—OH), alkoxyl, aryloxyl, aralkoxyl, nitro (—NO$_2$), cyano (—CN), amino (—NH$_2$), -N-substituted amino (—NHR"), -N,N-disubstituted amino (—N(R")R"), carboxyl (—COOH), —C(=O)R", —OR", —C(=O)OR", —NHC(=O)R", aminocarbonyl (—C(=O)NH$_2$), -N-substituted aminocarbonyl (—C(=O)NHR"), -N,N-disubstituted aminocarbonyl (—C(=O)N(R")R"), thiol, thiolato (SR"), sulfonic acid (SO$_3$H), phosphonic acid (PO$_3$H), S(=O)$_2$R", S(=O)$_2$NH$_2$, S(=O)$_2$NHR", S(=O)$_2$NR"R", NHS(=O)$_2$R", NR"S(=O)$_2$R", CF$_3$, CF$_2$CF$_3$, NHC(=(O)NHR", NHC(=O)NR"R", NR"C(=O)NHR", NR"C(=O)NR"R", and NR"C(=O)R", wherein each R" is independently H, alkyl, cycloalkyl, alkenyl, aryl, aralkyl, heteroaryl, or heterocycloalkyl;
or a stereoisomer, pharmaceutically acceptable salt, hydrate, solvate, acid salt hydrate or N-oxide thereof.

* * * * *